(12) United States Patent
Butcher

(10) Patent No.: US 8,222,273 B2
(45) Date of Patent: Jul. 17, 2012

(54) POLYMORPHIC FORM OF A [1,2,4]TRIAZOLE[4,3-A] PYRIDINE DERIVATIVE INFLAMMATORY DISEASES

(75) Inventor: Kenneth John Butcher, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 29 days.

(21) Appl. No.: 12/865,889

(22) PCT Filed: Jan. 28, 2009

(86) PCT No.: PCT/IB2009/050351
§ 371 (c)(1),
(2), (4) Date: Aug. 3, 2010

(87) PCT Pub. No.: WO2009/098612
PCT Pub. Date: Aug. 13, 2009

(65) Prior Publication Data
US 2011/0003848 A1   Jan. 6, 2011

Related U.S. Application Data

(60) Provisional application No. 61/025,879, filed on Feb. 4, 2008.

(51) Int. Cl.
*A61K 31/437* (2006.01)
*C07D 471/07* (2006.01)

(52) U.S. Cl. ....................... 514/303; 546/119

(58) Field of Classification Search .................. 514/303, 514/119
See application file for complete search history.

(56) References Cited

U.S. PATENT DOCUMENTS 7,511,057 B2   3/2009   Mathias et al. ............... 514/303

FOREIGN PATENT DOCUMENTS

| JP | 2002517487 | 6/2002 |
|---|---|---|
| JP | 2002530392 | 9/2002 |
| JP | 2007510715 | 4/2007 |
| WO | 9964405 | 12/1999 |
| WO | 0031055 | 6/2000 |
| WO | 2006008752 | 1/2006 |
| WO | WO2006018718 | 2/2006 |

OTHER PUBLICATIONS

Caira; Topics in Current chemistry, 1998, vol. 198, pp. 163-208.
Matsuoka et al., Pharm. Tech. Japan, vol. 19(6), pp. 91(955)-101(965), May 2003.

*Primary Examiner* — Jennifer M Kim
(74) *Attorney, Agent, or Firm* — A. David Joran; Mary J. Hosley

(57) ABSTRACT

The present invention relates to a polymorphic form B of Λ/-[3-tert-butyl-1-(3-chloro-4-hydroxyphenyl)-1H-pyrazol-5-yl]-N-{2-[(3-{2-[(2-hydroxyethyl)sulfanyl]phenyl}[1,2,4]triazolo[4,3-a]pyridin-6-yl)sulfanyl]benzyl}urea (I) as de-fined herein. This polymorph is useful in the treatment of various conditions, particularly in the treatment of inflammatory conditions such as chronic obstructive pulmonary disease.

4 Claims, 8 Drawing Sheets

POLYMORPHIC FORM OF A [1,2,4]TRIAZOLE[4,3-A] PYRIDINE DERIVATIVE INFLAMMATORY DISEASES

This application is a national stage filing of PCT/IB2009/050351 filed Jan. 28, 2009, which claims the benefit of Provisional Patent Application No. 61/025,879 filed Feb. 4, 2008.

The present invention relates to a polymorph of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea and to pharmaceutical compositions comprising and processes for making such a polymorph. The invention further relates to the use of the polymorph in the treatment of various conditions, particularly in the treatment of inflammatory conditions such as chronic obstructive pulmonary disease.

The compound N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea, having the structural formula (I):

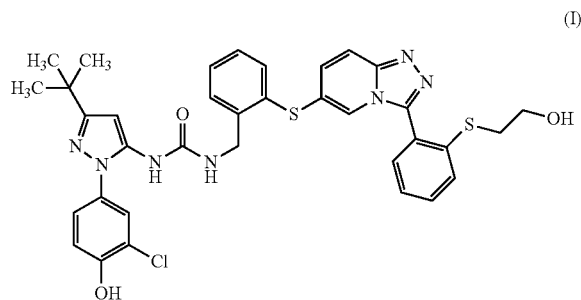

(I)

is disclosed in WO-A-06/018718 (see page 147, lines 19-20). The compound is one of a genus of compounds which are disclosed to be inhibitors of p38 MAP kinase and therefore useful in the treatment of allergic and non-allergic airways diseases such as chronic obstructive pulmonary disease (COPD).

If a compound is to be developed as a drug, it is important to provide a form of that compound (commonly known as a drug substance) which can be reliably prepared and purified on a large scale, which is stable and which does not degrade on storage. Such characteristics are normally found in a drug substance which is crystalline and of high melting point; a high-melting point crystalline solid tends to be easy to purify by re-crystallisation and stable on storage. Furthermore, the drug substance must be suitable for formulation in a dosage form chosen according to the intended route of administration. For formulation as a dry powder suitable for inhalation, non-hygroscopicity is particularly important in order to obtain good flow characteristics. Compatibility with conventional excipients in the inhalation field, such as lactose and starch, is a further mandatory requirement. Further, the drug substance will usually require processing in order to achieve a particle size suitable for inhalation and any crystalline form must be stable during such processing so that the properties of the final product are predictable and reliable. In short, whether or not a compound is suitable for commercialisation as a drug is dependent on finding a form of the compound with a unique combination of properties determined according to the intended route of administration.

It has now been possible to prepare a crystalline form of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea, known as form B, which has unique characteristics making it ideal for administration in a dry powder formulation. This polymorph is highly crystalline, has a melting point of about 226° C., is essentially non-hygroscopic and can be micronised by jet milling without inducing any change in crystalline form. It is a low-energy polymorph and does not convert readily into any other polymorphic or hydrated/solvated form of the compound. Furthermore, it shows good stability when blended with lactose monohydrate and stored under aggressive conditions of heat and humidity and the lactose blend aerosolises well when used in conjunction with standard dry powder inhalers.

Figure 1:
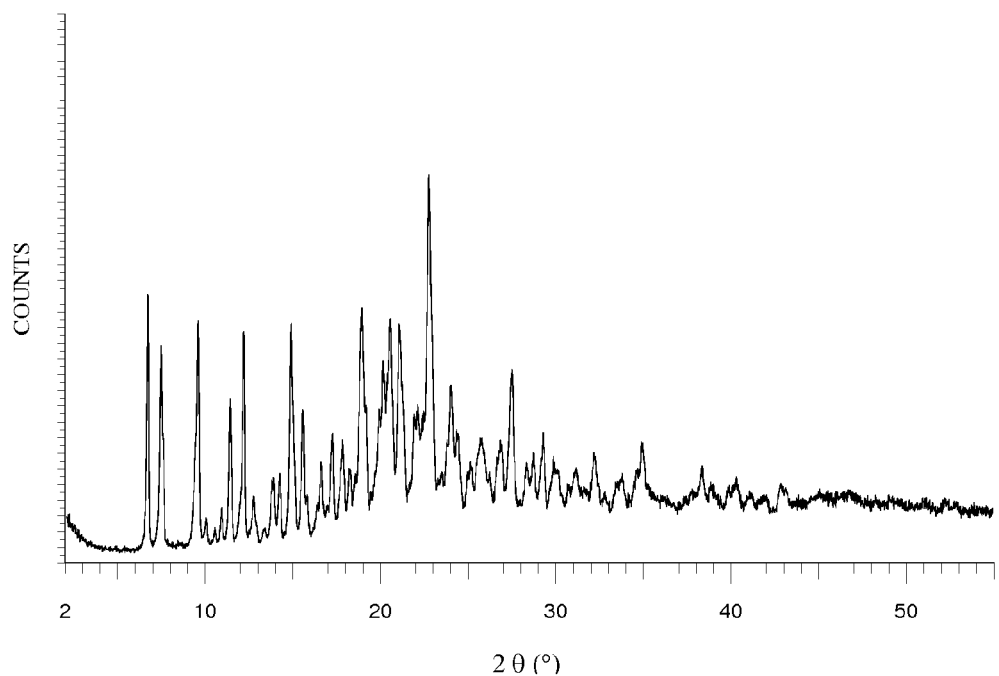
FIG. 1 shows an illustrative PXRD pattern for Form A.

The present invention therefore provides, in a first aspect, polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea.

The invention further provides: polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea for use as a medicament; polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea for use in treating a TNF-mediated or p38-mediated disease; the use of polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea for the manufacture of a medicament to treat a TNF-mediated or p38-mediated disease; a pharmaceutical composition comprising polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea and a pharmaceutically acceptable excipient; a pharmaceutical composition for the treatment of a TNF-mediated or p38-mediated disease comprising polymorphic form B of N-[3-tert-butyl-1-(3-chloro-4-hydroxyphenyl)-1H-pyrazol-5-yl]-N'-{2-[(3-{2-[(2-hydroxyethyl) sulfanyl]phenyl}[1,2,4]triazolo[4,3-a]pyridin-6-yl)sulfanyl]benzyl}urea; and a method of treating a TNF-mediated or p38-mediated disease in a mammal comprising administering to the mammal in need thereof a therapeutically effective amount of polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea. Preferred diseases are inflammatory respiratory diseases such as asthma and COPD, particularly COPD.

When N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea is prepared, for instance using the routes set out in WO-A-06/018718, it is obtained in either an amorphous form or a crystalline form known as form A. Crystallisation of the amorphous form from standard organic solvents also provides form A. We have surprisingly found, however, that form A is not the only crystalline form of the compound. Using specially developed conditions, form A can be converted to a second crystalline form known as form B. Furthermore, form B is a more stable, lower-energy form of the compound which has particularly desirable properties making it an ideal drug substance for administration in a dry powder formulation.

In order to convert form A to form B it is necessary to take a take crystals of form A having a purity of at least 95% and reflux them in an organic solvent for an extended period. The progress of the conversion can be can monitored by analysing samples according to standard techniques described below such as powder X-ray diffraction. A reaction time of at least 12 hours, typically a reaction time of from 12 to 48 hours, is usually required for complete conversion, but the reaction can be accelerated by adding a seed crystal of the form B product. The use of a seed, however, is not crucial to the success of the reaction. On the other hand, the purity of the starting material is an important factor. If form A having a lower purity (e.g. 70-80%) is subjected to the same conditions then conversion will not occur and the product will be unchanged form A. This is the case even when the reaction is subjected to long reaction times in the presence of a seed. A sample of form A having the required degree of purity can be prepared by simple recrystallisation from a variety of organic solvents. The use of an elevated temperature is also important since recrystallisation of form A at low temperatures does not lead to conversion to form B. The reaction is typically conducted at the reflux temperature of an organic solvent having a boiling point of greater than about 60° C. (at atmospheric pressure). Methanol is a preferred solvent.

The invention therefore also provides a process for the preparation of N-[3-tert-butyl-1-(3-chloro-4-hydroxyphenyl)-1H-pyrazol-5-yl]-N'-{2-[(3-{2-[(2-hydroxyethyl) sulfanyl]phenyl}[1,2,4]triazolo[4,3-a]pyridin-6-yl)sulfanyl]benzyl}urea form B which comprises heating a slurry of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea form A, of at least 95% purity, at reflux, in an organic solvent having a boiling point of greater than about 60° C.

N-[3-tert-Butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea may be prepared by constructing the urea group, with a carbonyl source such as phenylchloroformate and relevant amine components, as disclosed on pages 29 and 30 of WO-A-06/018718. A preferred process is set out in Scheme 1 below, wherein Ph is phenyl and $P^1$ and $P^2$ are both suitable oxygen protecting groups. Examples of such suitable oxygen protecting groups may be found in 'Protective Groups in Organic Synthesis' by Theodora Greene and Peter Wuts (third edition, 1999, John Wiley & Sons). Preferred protecting groups are tri($C_1$-$C_6$)alkylsilyl groups. Most preferably, $P^1$ and $P^2$ are both tri-isopropylsilyl.

Scheme 1

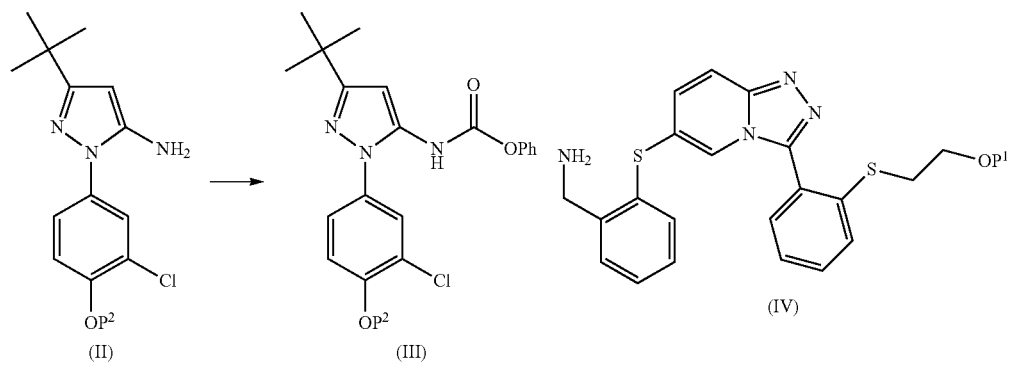

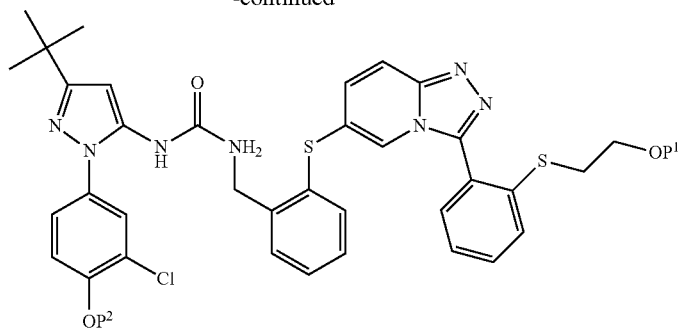

(V)

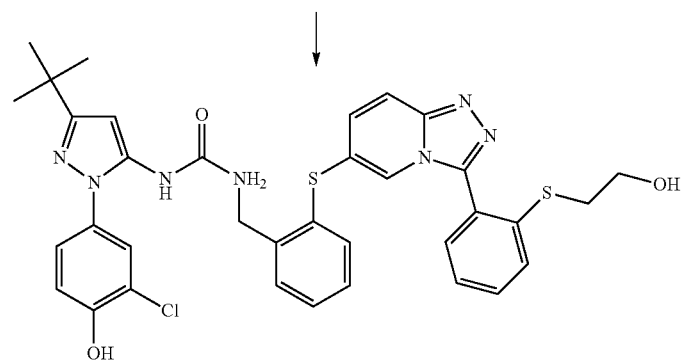

(I)

As shown in Scheme 1, a compound of formula (I) may be prepared by deprotecting a compound of formula (V). Suitable conditions, which must be chosen according to the choices made for $P^1$ and $P^2$, are described in 'Protective Groups in Organic Synthesis' referenced above. If, for example, $P^1$ and $P^2$ are both tri-isopropylsilyl, then a solution of the compound of formula (V) in a suitable organic solvent, such as methanol, may be treated with an acid, such as hydrochloric acid, preferably at an elevated temperature such as about 50° C.

A compound of formula (V) may be prepared by reacting a carbamate of formula (III) with an amine of formula (IV). Typically, a solution of the two reactants in a suitable organic solvent, such as toluene, is treated with a base, such as N,N-diisopropylethylamine and allowed to react at room temperature.

A compound of formula (III) may be prepared by reacting an amine of formula (II) with phenyl chloroformate. Typically, a solution of the compound of formula (II) in a suitable solvent, such as ethyl acetate, is treated with phenyl chloroformate and a base, such as sodium bicarbonate.

A compound of formula (II) can be prepared by the route set out in Scheme 2 below, wherein $P^2$ is a suitable oxygen protecting group. Examples of suitable oxygen protecting groups may be found in 'Protective Groups in Organic Synthesis' by Theodora Greene and Peter Wuts (third edition, 1999, John Wiley & Sons). A preferred protecting group is a tri($C_1$-$C_6$)alkylsilyl group. Most preferably, $P^2$ is tri-isopropylsilyl.

Scheme 2

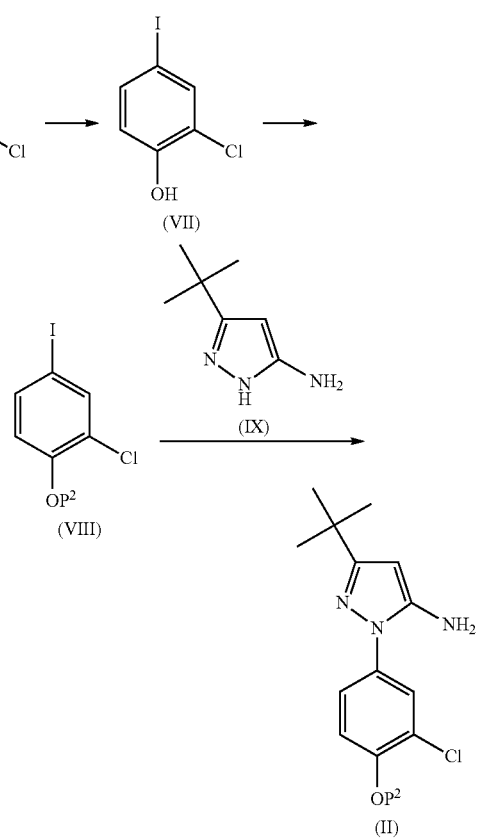

A compound of formula (II) may be prepared by coupling an iodide of formula (VIII) with a pyrazole of formula (IX). Typically, a solution of the reactants in a suitable organic solvent, such as toluene, is treated with an organometallic catalyst, such as copper(I) iodide/trans-N,N'dimethylcyclohexane-1,2-diamine and a base, such as potassium carbonate, and heated, e.g. to about 111° C.

A compound of formula (VIII) may be prepared by protecting the hydroxyl group in a compound of formula (VII). Suitable conditions, which must be chosen according to the choice made for $P^2$, are described in 'Protective Groups in Organic Synthesis' referenced above. If, for example, $P^2$ is tri-isopropylsilyl, then a solution of the compound of formula (VII) in a suitable organic solvent, such as toluene, may be treated with tri-isopropylsilyl chloride and a base, such as triethylamine.

A compound of formula (VII) may be prepared by iodination of 2-chlorophenol. Typically, a solution of 2-chlorophenol in a suitable organic solvent is treated with a mixture of sodium iodide and sodium hypochlorite.

A compound of formula (IV) can be prepared by the route set out in Scheme 3 below, wherein $P^1$ is a suitable oxygen protecting group. Examples of suitable oxygen protecting groups may be found in 'Protective Groups in Organic Synthesis' by Theodora Greene and Peter Wuts (third edition, 1999, John Wiley & Sons). A preferred protecting group is a tri($C_1$-$C_6$)alkylsilyl group. Most preferably, $P^1$ is tri-isopropylsilyl.

Scheme 3

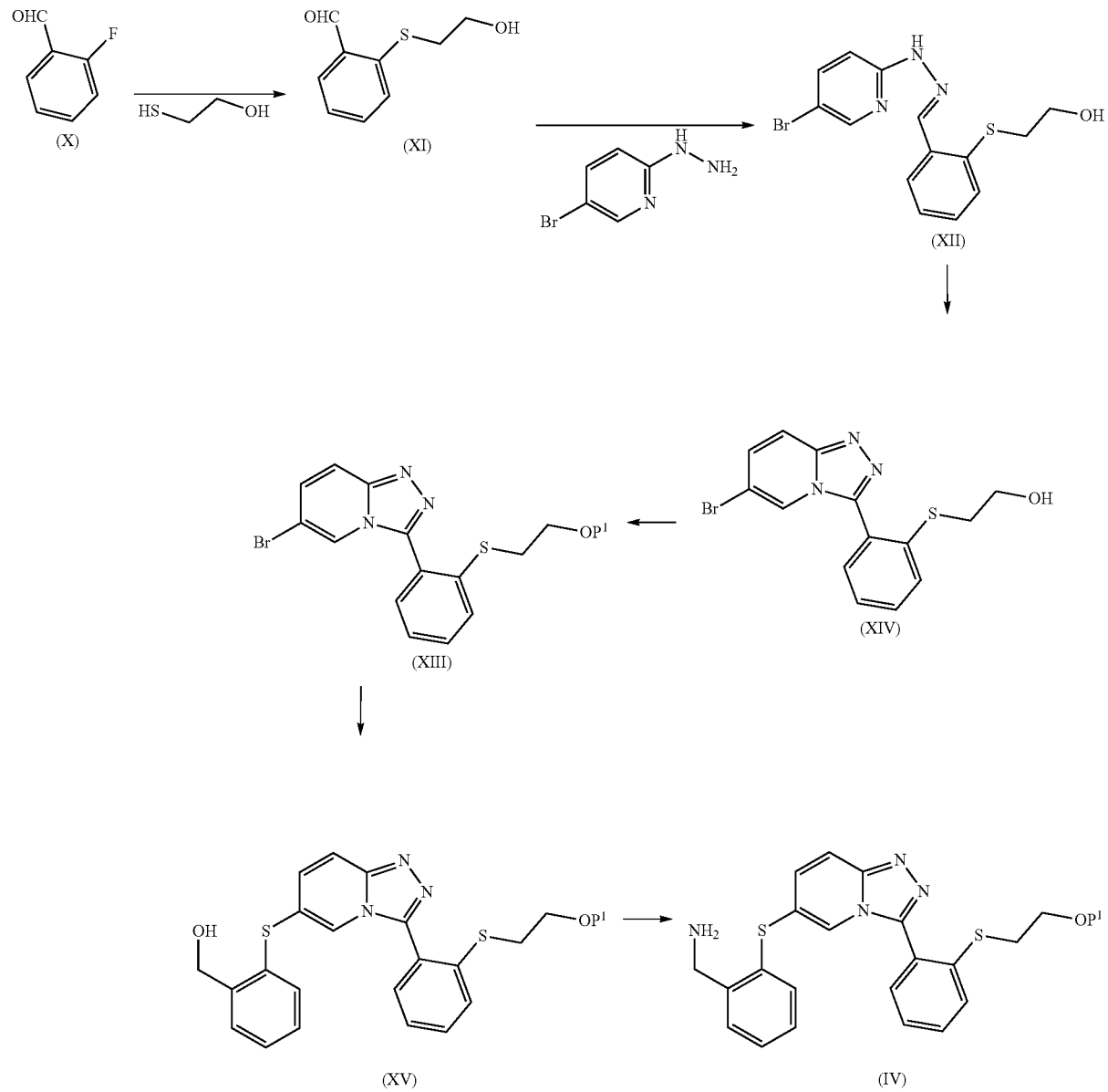

A compound of formula (IV) may be prepared by activation of the hydroxyl group of a compound of formula (XV) to nucleophilic substitution and displacement with ammonia. In a typical procedure, a solution of the compound of formula (XV) in a suitable organic solvent, such as toluene, is treated with an activating agent, such as methanesulphonyl anhydride, and a base, such as triethylamine, in order to activate the hydroxyl group. The reaction mixture is then treated with ammonia, preferably a solution of ammonia in methanol.

A compound of formula (XV) may be prepared by displacing the bromide atom in a compound of formula (XIII) with (2-sulfanylphenyl)methanol. The reaction is catalysed by a transition metal complex such as [1,1'-bis(diphenylphosphino)ferrocene]dichloro palladium (II). In a typical procedure, a solution or slurry of the compound of formula (XIII) in a suitable organic solvent, such as toluene, is treated with (2-sulfanylphenyl)methanol, [1,1'-bis(diphenylphosphino)ferrocene]dichloro palladium (II) and a base, such as sodium tert-butyloxide and heated, e.g. to about 111° C.

A compound of formula (XIII) can be prepared by protecting the hydroxyl group in a compound of formula (XIV). Suitable conditions, which must be chosen according to the choice made for $P^1$, are described in 'Protective Groups in Organic Synthesis' referenced above. If, for example, $P^1$ is tri-isopropylsilyl, then a solution or slurry of the compound of formula (XIV) in a suitable organic solvent, such as 2-methyltetrahydrofuran, may be treated with tri-isopropylsilyl chloride and a base, such as imidazole. The reaction is preferably heated at about 50° C.

A compound of formula (XIV) may be prepared by cyclisation of a compound of formula (XII). The cyclisation is preferably achieved by treating a solution of a compound of formula (XII) in a suitable solvent, such as dichloromethane, with diacetoxyiodobenzene and methanol.

A compound of formula (XII) may be prepared by condensing the aldehyde of formula (XI) with 5-bromopyridin-2-ylhydrazine. The hydrazine can be prepared using the procedures set out in WO-A-06/018718 (see preparation 25). Typically, a solution of the reactants in a suitable organic solvent, such as propionitrile, is heated, e.g. at about 85° C.

A compound of formula (XI) may be prepared by displacing the fluoride atom of 2-fluorobenzaldehyde with 2-mercaptoethanol. Typically, a solution of the reactants in a suitable organic solvent, such as propionitrile, is treated with a base, such as potassium carbonate and the reaction mixture is heated, e.g. at about 85° C.

The present invention includes all isotopically-labelled forms of the polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea provided by the invention. In an isotopically-labelled form, one or more atoms are replaced by an atom or atoms having the same atomic number, but an atomic mass or mass number different from the atomic mass or mass number which predominates in nature.

Suitable isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O; and sulphur, such as $^{35}$S. Certain isotopically-labelled compounds, such as those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and, $^{13}$N, can be useful in Positron Emission Topography (PET) studies for examining substrate receptor occupancy. Isotopically-labeled compounds can generally be prepared by conventional techniques known to those skilled in the art or by processes analogous to those described in the accompanying experimental section using an appropriate isotopically-labeled reagent in place of the non-labeled reagent previously employed.

The polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea provided by the invention is an inhibitor of p38 mitogen activated protein kinase (p38 MAP kinase), particularly p38α MAP kinase and consequently inhibits the production of interleukin-1 (IL-1), interleukin-8 (IL-8) and tumor necrosis factor (TNF). It may be useful the treatment of the following conditions:

Treatable obstructive, restrictive or inflammatory airways diseases of whatever type, etiology, or pathogenesis, in particular an obstructive, restrictive or inflammatory airways disease such as:
asthma, in particular atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or inapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma;
bronchial hyper-responsivity to environmental agents;
rhinitis or sinusitis of whatever type, etiology, or pathogenesis, in particular seasonal allergic rhinitis, perennial allergic rhinitis, perennial rhinitis, vasomotor rhinitis, post-nasal drip, purulent or nonpurulent sinusitis, acute or chronic sinusitis and ethmoid, frontal, maxillary, or sphenoid sinusitis;
chronic obstructive pulmonary disease (COPD), chronic obstructive lung disease (COLD), chronic obstructive airways disease (COAD) or small airways obstruction of whatever type, etiology, or pathogenesis, in particular chronic bronchitis, pulmonary emphysema, bronchiectasis, cystic fibrosis, bronchiolitis obliterans, bronchiolitis obliterans organizing pneumonia (BOOP), chronic organizing pneumonia (COP), bronchiolitis fibrosa obliterans, follicular bronchiolitis or dyspnea associated therewith;
bronchitis of whatever type, etiology, or pathogenesis, in particular acute bronchitis, acute laryngotracheal bronchitis, arachidic bronchitis, catarrhal bronchitis, croupus bronchitis, chronic bronchitis, dry bronchitis, infectious asthmatic bronchitis, productive bronchitis, *staphylococcus* or streptococcal bronchitis and vesicular bronchitis;
bronchiectasis of whatever type, etiology, or pathogenesis, in particular cylindric bronchiectasis, sacculated bronchiectasis, fusiform bronchiectasis, capillary bronchiectasis, cystic bronchiectasis, cystic fibrosis, Kartageners's syndrome, dry bronchiectasis or follicular bronchiectasis;

pulmonary eosinophilic syndromes of whatever type, etiology, or pathogenesis, in particular acute eosinophilic pneumonia (idiopathic or due to drugs or parasites), simple pulmonary eosinophilia, Loeffler's syndrome, tropical pulmonary eosinophilia, chronic eosinophilic pneumonia, allergic bronchopulmonary mycosis, allergic bronchopulmonary aspergillosis (ABPA), Churg-Strauss syndrome or idiopathic hypereosinophilic syndrome;

interstitial lung diseases (ILD) or pulmonary fibrosis of whatever type, etiology, or pathogenesis, in particular idiopathic pulmonary fibrosis, crytogenic fibrosing alveolitis, fibrosing alveolitis, ILD or pulmonary fibrosis associated with connective tissue disease (systemic lupus erythematosis, mixed connective tissue disease, polymyositis, dermatomyositis, Sjörgen's syndrome, systemic sclerosis, scleroderma, rheumatoid arthritis), usual interstitial pneumonia (UIP), desquamative interstitial pneumonia (DIP), granulomatous lung disease, sarcoidosis, Wegener's granulomatosis, histiocytosis X, Langerhan's cell granulomatosis, hypersensitivity pneumonitis, extrinsic allergic alveolitis, silicosis, chronic eosinophilic pneumonia, lymphangiolyomatosis, drug-induced ILD or pulmonary fibrosis, radiation-induced ILD or pulmonary fibrosis, alveolar proteinosis, graft-versus-host-disease (GVHD), lung transplant rejection, ILD or pulmonary fibrosis due to environmental/occupational exposure, BOOP, COP, bronchiolitis fibrosa obliterans, follicular bronchiolitis, idiopathic acute interstitial pneumonitis (Hamman Rich syndrome) or alveolar hemorrhage syndromes;

pneumoconiosis of whatever type, etiology, or pathogenesis, in particular aluminosis or bauxite workers' disease, anthracosis or miners' asthma, progressive massive fibrosis (PMF), asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma or talc pneumoconiosis;

Acute Respiratory Distress Syndrome (ARDS), adult respiratory distress syndrome or acute lung injury of whatever type, etiology, or pathogenesis;

aspiration disorders of whatever type, etiology, or pathogenesis leading to aspiration pneumonitis or aspiration pneumonia;

alveolar hemorrhage of whatever type, etiology, or pathogenesis, in particular a member of the group consisting of idiopathic pulmonary hemosiderosis, alveolar hemorrhage due to drugs or other exogenous agents, alveolar hemorrhage associated with HIV or bone marrow transplant or autoimmune alveolar hemorrhage (e.g. associated with systemic lupus erythematosis, Goodpasture's syndrome, Wegener's granulomatosis, microscopic polyangiitis, Churg-Strauss syndrome, pauci-immune glomerulonephritis);

acute or chronic laryngitis or pharyngitis;

cough of whatever type, etiology, or pathogenesis in particular idiopathic cough or cough associated with gastro-esophageal reflux disease (GERD), drugs, bronchial hyper-responsivity, asthma, COPD, COLD, COAD, bronchitis, bronchiectasis, pulmonary eosinophilic syndromes, pneumoconiosis, interstitial lung disease, pulmonary fibrosis, aspiration disorders, rhinitis, laryngitis or pharyngitis;

anaphylaxis and type 1 hypersensitivity reactions of whatever aetiology;

atopic, allergic, autoimmune or inflammatory skin disorders of whatever type, etiology, or pathogenesis, in particular atopic dermatitis, allergic dermatitis, contact dermatitis, allergic or atopic eczema, lichen planus, mastocytosis, erythema nodosum, erythema multiforme, benign familial pemphigus, pemphigus erythematosus, pemphigus foliaceus, and pemphigus vulgaris, bullous pemphigoid, epidermolysis bullosa, dermatitis hepetiformis, psoriasis, immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria or papular urticaria;

conjunctivitis of whatever type, etiology, or pathogenesis, in particular actinic conjunctivitis, acute catarrhal conjunctivitis, acute contagious conjunctivitis, allergic conjunctivitis, atopic conjunctivitis, chronic catarrhal conjunctivitis, purulent conjunctivitis or vernal conjunctivitis;

multiple sclerosis of whatever type, etiology, or pathogenesis, in particular primary progressive multiple sclerosis or relapsing remitting multiple sclerosis;

autoimmune/inflammatory diseases of whatever type, etiology, or pathogenesis, in particular autoimmune hematological disorders, hemolytic anemia, aplastic anemia, pure red cell anemia, idiopathic thrombocytopenic purpura, rheumatoid arthritis, systemic lupus erythematosus, scleroderma, systemic sclerosis, oolymyalgia rheumatica, dermatomyositis, polymyositis, polychondritis, Wegner's granulomatosis, chronic active hepatitis, myasthenia gravis, Stevens-Johnson syndrome, idiopathic sprue, autoimmune inflammatory bowel diseases, Crohn's disease, ulcerative colitis, endocrine opthalmopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, glomerulonephritis with or without nephrotic syndrome, acute glomerulonephritis, idiopathic nephrotic syndrome, minimal change nephropathy, autoimmune disorders associated with interstitial lung disease and/or pulmonary fibrosis or autoimmune or inflammatory skin disorders;

inflammatory bowel disease (IBD) of whatever type, etiology, or pathogenesis, in particular collagenous colitis, colitis polyposa, transmural colitis, ulcerative colitis or Crohn's disease (CD);

pulmonary hypertension of whatever type, etiology or pathogenesis including pulmonary arterial hypertension, pulmonary venous hypertension, pulmonary hypertension associated with disorders of the respiratory system and/or hypoxemia, pulmonary hypertension due to chronic thrombotic and/or embolic disease and pulmonary hypertension due to disorders directly affecting the pulmonary vasculature;

arthritis of whatever type, etiology, or pathogenesis, in particular rheumatoid arthritis, osteorthritis, gouty arthritis, pyrophosphate arthropathy, acute calcific periarthritis, chronic inflammatory arthritis, arthritis associated with a connective tissue disorder (e.g. systemic lupus erythematosis, polymyositis, dermatomyositis, systemic sclerosis, scleroderma), sarcoidosis, polymyalgia rheumatica, degenerative arthritis, infectious arthritis, Lyme arthritis, proliferative arthritis, psoriatic arthritis, ankylosing spondylitis, cervical spondylosis, vertebral arthritis, juvenile arthritis (Still's disease), amyloidosis, ankylosing vertebral hyperostosis (Forrestier's disease), Behçet's syndrome, drug-induced arthritis, familial Mediterranean fever, hypermobility syndrome, osteochondritis dessicans, osteochondromatosis, palindromic rheumatism, pigmented villonodular synovitis, relapsing polychondritis, temporomandibular pain dysfunction syndrome or arthritis associated with hyperlipidemia;

an eosinophil-related disorder of whatever type, etiology, or pathogenesis, in particular pulmonary eosinophilic syndromes, aspergilloma, granulomas containing eosinophils, allergic granulomatous angiitis or Churg-Strauss syndrome, polyarteritis nodosa (PAN) or systemic necrotizing vasculitis;

uveitis of whatever type, etiology, or pathogenesis, in particular inflammation of all or part of the uvea, anterior uveitis, iritis, cyclitis, iridocyclitis, granulomatous uveitis, nongranulomatous uveitis, phacoantigenic uveitis, posterior uveitis, choroiditis or chorioretinitis;

septic shock of whatever type, etiology, or pathogenesis;

disorders of bone deposition/resorption, including osteoporosis and osteopenia;

lymphoproliferative disorders (e.g. lymphoma, myeloma);

HIV or AIDs related disorders;

infection, especially infection due to viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including *Herpes zoster* and *Herpes simplex;* yeast and fungal infections wherein the yeast or fungus is sensitive to upregulation by TNF-α or elicits TNF-α production in the host, e.g., fungal meningitis, particularly when administered in conjunction with other drugs of choice for the treatment of systemic yeast and fungus infections, including but are not limited to, polymixins (e.g. Polymycin B), imidazoles (e.g. clotrimazole, econazole, miconazole, and ketoconazole), triazoles (e.g. fluconazole and itranazole) and amphotericins (e.g. Amphotericin B and liposomal Amphotericin B); and Mycobacterial infections e.g. due to *mycobacterium tuberculosis.*

The polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea provided by the invention (henceforth referred to as the compound of the invention) may be administered alone but will generally be administered as a formulation in association with one or more pharmaceutically acceptable excipients. The term 'excipient' is used herein to describe any ingredient other than the compound of the invention. The choice of excipient will to a large extent depend on factors such as the particular mode of administration, the effect of the excipient on solubility and stability, and the nature of the dosage form.

Pharmaceutical compositions suitable for the delivery of the compound of the invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compound of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the compound of the invention may make up from 1 weight % to 80 weight % of the dosage form, more typically from 5 weight % to 60 weight % of the dosage form.

In addition, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are also generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc.

When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible tablet ingredients include anti-oxidants, colouring agents, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller compaction to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

The compound of the invention may also be orally administered in the form of a consumable oral film for human or veterinary use. Such a film is typically a pliable water-soluble or water-swellable thin film dosage form which may be rapidly dissolving or mucoadhesive and typically comprises the compound of the invention, a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible film ingredients include anti-oxidants, colouring agents, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuum drying.

Solid formulations for oral administration may be formulated to be immediate and/or modified release. Modified release includes delayed, sustained, pulsed, controlled, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO-A-00/35298.

The compound of the invention may also be administered directly into the blood stream, into muscle, or into an internal organ. Such parenteral administration may be via the intravenous, intraarterial, intraperitoneal, intrathecal, intraventricular, intraurethral, intrasternal, intracranial, intramuscular or subcutaneous route. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

Formulations for parenteral administration may be formulated to be immediate and/or modified release. Modified release includes delayed, sustained, pulsed, controlled, targeted and programmed release. Thus compounds of the invention may be formulated as a solid, semi-solid or thixotropic liquid for administration as an implanted depot providing modified release of the compound of the invention. Examples of such formulations include drug-coated stents and poly(d/-lactic-coglycolic)acid (PGLA) microspheres.

The compound of the invention may also be administered topically to the skin or mucosa, i.e. dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J. Pharm. Sci., 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™) injection.

Formulations for topical administration may be formulated to be immediate and/or modified release. Modified release includes delayed, sustained, pulsed, controlled, targeted and programmed release.

The compound of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin. Administration in the form of a dry powder from a dry powder inhaler is a particularly preferred form of delivery.

The pressurised container, pump, spray, atomizer or nebuliser contains a solution or suspension of the compound of the invention comprising, for example, ethanol, aqueous ethanol or a suitable alternative agent for dispersing, solubilising or extending release of the active, a propellant(s) as solvent and an optional surfactant, such as sorbitan trioleate, oleic acid or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise the compound of the invention, propylene glycol, sterile water, ethanol and sodium chloride. Alternative solvents which may be used instead of propylene glycol include glycerol and polyethylene glycol.

Suitable flavouring agents, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release includes delayed, sustained, pulsed, controlled, targeted and programmed release.

In the case of dry powder inhalers and aerosols, the dosage unit may be determined by means of a valve which delivers a metered amount. The overall daily dose may be administered in a single dose or, more usually, as divided doses throughout the day.

The compound of the invention may be administered rectally or vaginally, in the form, for example, of a suppository, pessary or enema. Cocoa butter is a traditional suppository base, but various alternatives may be used as appropriate.

The compound of the invention may also be administered by the ocular or aural route.

The compound of the invention may be combined with a soluble macromolecular entity, such as a cyclodextrin or a suitable derivative thereof or a polyethylene glycol-containing polymer, in order to improve its solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in WO-A-91/11172, WO-A-94/02518 and WO-A-98/55148.

For administration to human patients, the total daily dose of the compound of the invention will typically be in the range 0.002 mg/kg to 100 mg/kg depending, of course, on the mode of administration. The total daily dose may be administered in single or divided doses and may, at the physician's discretion, fall outside of the typical range given herein.

For the avoidance of doubt, references herein to "treatment" include references to curative, palliative and prophylactic treatment.

Inhibitors of p38 MAP kinase, such as the compound of the invention, may advantageously be administered in combination with one or more other therapeutic agents, particularly in the treatment of respiratory diseases such as chronic obstructive pulmonary disease. Examples of such further therapeutic agents include: (i) 5-lipoxygenase (5-LO) inhibitors or 5-lipoxygenase activating protein (FLAP) antagonists; (ii) leukotriene antagonists (LTRAs) including antagonists of $LTB_4$, $LTC_4$, $LTD_4$, and $LTE_4$; (iii) histamine receptor antagonists including $H_1$, $H_3$ and $H_4$ antagonists; (iv) $\alpha_1$- and $\alpha_2$-adrenoceptor agonist vasoconstrictor sympathomimetic agents for nasal decongestant use; (v) muscarinic $M_3$ receptor antagonists or anticholinergic agents; (vi) PDE inhibitors, e.g. $PDE_3$, $PDE_4$ and $PDE_5$ inhibitors; (vii) theophylline; (viii) sodium cromoglycate; (ix) COX inhibitors both non-selective and selective COX-1 or COX-2 inhibitors (NSAIDs); (x) oral and inhaled glucocorticosteroids, such as DAGR (dissociated agonists of the corticoid receptor); (xi) monoclonal antibodies active against endogenous inflammatory entities; (xii) anti-tumor necrosis factor (anti-TNF-$\alpha$) agents; (xiii) adhesion molecule inhibitors including VLA-4 antagonists; (xiv) kinin-$B_1$- and $B_2$-receptor antagonists; (xv) immunosuppressive agents; (xvi) inhibitors of matrix metalloproteases (MMPs); (xvii) tachykinin $NK_1$, $NK_2$ and $NK_3$ receptor antagonists; (xviii) elastase inhibitors; (xix) adenosine $A_{2a}$ receptor agonists; (xx) inhibitors of urokinase; (xxi) compounds that act on dopamine receptors, e.g. $D_2$ agonists; (xxii) modulators of the NFκ☐ pathway, e.g. IKK inhibitors; (xxiii) modulators of cytokine signaling pathways such as a p38 MAP kinase or JAK kinase inhibitor; (xxiv) agents that can be classed as mucolytics or anti-tussive; (xxv) antibiotics; (xxvi) HDAC inhibitors; (xxvii) PI3 kinase inhibitors; (xxviii) $\beta_2$ agonists; and (xxix) dual compounds active as $\beta_2$ agonists and muscarinic $M_3$ receptor antagonists. Preferred examples of such therapeutic agents include: (a) glucocorticosteroids, in particular inhaled glucocorticosteroids with reduced systemic side effects, flunisolide, triamcinolone acetonide, beclomethasone dipropionate, budesonide, fluticasone propionate, ciclesonide, and mometasone furoate; (b) muscarinic $M_3$ receptor antagonists or anticholinergic agents including ipratropium salts such as the bromide, tiotropium salts such as the bromide, oxitropium salts such as the bromide, perenzepine and telenzepine; and (c) $\beta_2$ agonists including salbutamol, terbutaline, bambuterol, fenoterol, salmeterol, formoterol, tulobuterol. Any of the agents specifically mentioned may optionally be used in the form of a pharmaceutically acceptable salt.

Where it is desirable to administer a combination of active compounds, two or more pharmaceutical compositions, at least one of which contains the compound of the invention, may conveniently be combined in the form of a kit suitable for co-administration.

Such a kit comprises two or more separate pharmaceutical compositions, at least one of which contains the compound of the invention, and means for separately retaining said compositions, such as a container, divided bottle, or divided foil packet. An example of such a kit is the familiar blister pack used for the packaging of tablets, capsules and the like.

Such a kit is particularly suitable for administering different dosage forms, for example, oral and parenteral dosage forms, for administering the separate compositions at different dosage intervals, or for titrating the separate compositions against one another. To assist compliance, the kit typically comprises directions for administration and may be provided with a so-called memory aid.

PREPARATIVE EXAMPLES

Example 1

Preparation of (2-chloro-4-iodophenoxy)(triisopropyl)silane

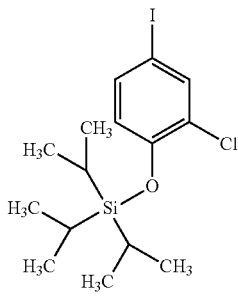

To a solution of 2-chloro-4-iodophenol (351.2 g, 1.38 moles) in toluene (1750 ml) under nitrogen, was added triethylamine (168 g, 1.66 moles), dimethylaminopyridine (8.5 g, 0.069 moles) and chlorotriisopropylsilane (320 g, 1.66 moles), then stirred for 16 hours. After this time the reaction was quenched by the addition of aqueous hydrochloric acid (2M, 1000 ml) and the organic phase washed with water (1000 ml). The solution was dried by azeotropic distillation of toluene, to give the title compound as a clear oil (497 g, 87%).

$^1$H-NMR (300 MHz, CDCl$_3$): δ=0.98-1.12 (m, 21H), 6.65-6.68 (d, 1H), 7.38-7.41 (d, 1H), 7.66 (s, 1H).

Example 2

Preparation of 3-tert-butyl-1-[3-chloro-4-(triisopropylsilyloxy)phenyl]-1H-pyrazol-5-amine

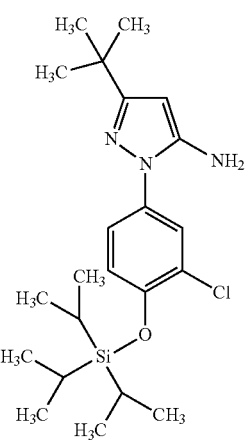

To a solution of aryl iodide of Example 1 (493.6 g, 1.202 moles) in toluene (1000 ml) under nitrogen, was added 3-tert-butyl-1H-pyrazol-5-amine (184.2 g, 1.322 moles) followed by trans-N,N'dimethylcyclohexane-1,2-diamine (16.2 g, 0.240 moles), potassium carbonate (348 g, 2.52 moles) and copper (I) iodide (11.6 g, 0.061 moles). The mixture was heated at 111° C. for 16 hours. After this time the reaction was cooled to 20° C., and partitioned with water (1500 ml) and ethyl acetate (1500 ml). The organic phase was sequentially washed with 10% w/v aqueous citric acid solution (1500 ml) and water (1500 ml). Solvent was distilled under reduced pressure and replaced by n-heptane (1500 ml). The solution was cooled to 5° C. granulated for 16 hours. The solid was collected by filtration to give the title compound as a brown solid (334 g, 65%).

$^1$H-NMR (300 MHz, CDCl$_3$): δ=1.14-1.17 (d, 18H), 1.28-1.39 (m, 3H), 1.32 (s, 9H), 5.51 (s, 1H), 6.95-6.98 (d, 1H), 7.32-7.35 (d, 1H), 7.59 (s, 1H).

Example 3

Preparation of phenyl{3-tert-butyl-1-[3-chloro-4-(triisopropylsilyloxy)phenyl]-1H-pyrazol-5-yl}carbamate

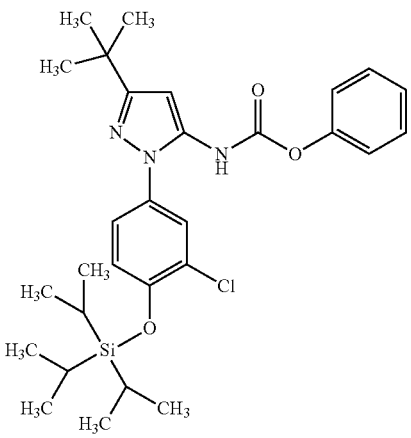

To a solution of aminopyrazole of Example 2 (325 g, 0.707 moles) in ethyl acetate (1625 ml) under nitrogen, was added sodium bicarbonate aqueous solution (8% w/v, 1625 ml, 1.54 moles). Phenyl chloroformate (145 ml, 1.155 moles) was added over 15 minutes and stirred at 20° C. for 16 hours. The organic phase was separated and washed with water (1625 ml). Solvent was distilled under reduced pressure and replaced by n-heptane (1625 ml). The solution was cooled to 5° C. and granulated for 3 hours. The solid was collected by filtration to give the title compound as a white solid (368 g, 88%).

$^1$H-NMR (300 MHz, CDCl$_3$): δ=1.16-1.19 (d, 18H), 1.30-1.42 (m, 3H), 6.45 (s, 1H), 7.01-7.04 (d, 1H), 7.14-7.17 (m, 2H), 7.24-7.30 (m, 2H), 7.38-7.43 (m, 2H), 7.55 (s, 1H).

Example 4

Preparation of 2-[(2-hydroxyethyl)sulfanyl]benzaldehyde

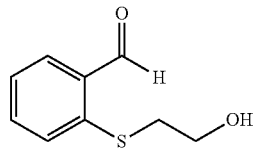

To a slurry of potassium carbonate (362 g, 2.62 moles) in propionitrile (1000 ml) under nitrogen, was added 2-mercaptoethanol (184 ml, 2.618 moles) as a solution in propionitrile (750 ml). 2-Fluorobenzaldehyde (250 g, 2.014 moles) was added as a solution in propionitrile (750 ml) and heated at 85° C. for 18 hours. The reaction was cooled to 20° C. and sequentially washed with water (1500 ml), 1M sodium hydroxide solution (500 ml) and water (1000 ml). The final solution was dried by azeotropic distillation to leave the title compound as a clear, yellow solution in propionitrile (4250 ml). A small sample was concentrated for yield calculation (348.7 g, 95%).

$^1$H-NMR (300 MHz, d6-DMSO): δ=3.08-3.12 (t, 2H), 3.6-3.67 (m, 2H), 4.96-5.00 (t, 1H), 7.35-7.40 (t, 1H), 7.55-7.65 (m, 2H), 7.85-7.88 (d, 1H), 10.24 (s, 1H).

Example 5

Preparation of 2-[(2-{[5-bromopyridin-2-yl)hydrazono]methyl}phenyl) sulfanyl]ethanol

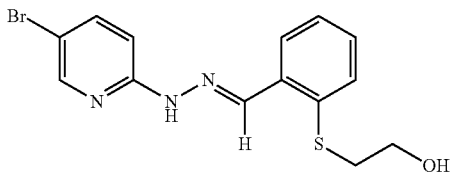

To a solution of aldehyde of Example 4 (314.0 g, 1.723 moles) in propionitrile (3770 ml) was added 5-bromopyridin-2-yl hydrazine under nitrogen. The mixture was heated at 85° C. for 2 hours, then cooled to 5° C. and granulated for 18 hours. The solid was collected by filtration to yield the title compound as a white solid (500.3 g, 82%).

$^1$H-NMR (300 MHz, CDCl$_3$): δ=3.07-3.11 (t, 2H), 7.30-7.34 (m, 2H), 7.49-7.52 (m, 1H), 7.70-7.73 (d, 1H), 7.97-8.00 (m, 1H), 8.24 (s, 1H), 8.43 (s 1H), 8.77 (s, 1H.

Example 6

Preparation of 2-{[2-(6-bromo[1,2,4]triazolo[4,3-a]pyridin-3-yl)phenyl]sulfanyl}ethanol

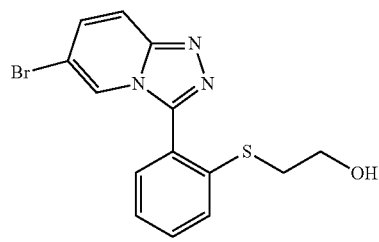

To a solution of hydrazone of Example 5 (200 g, 0.5678 moles) in dichloromethane (2500 ml) was added diacetoxyiodobenzene (192 g, 0.5962 moles). The mixture was cooled to 5° C. and methanol (280 ml) was added over 20 minutes then warmed to 20° C. and stirred for 2 hours. The mixture was cooled to 5° C. and 2M sodium hydroxide solution (600 ml) was added over 15 minutes. The organic layer was washed with water (800 ml) and solvent was distilled and replaced with fresh acetonitrile to give a final volume of 800 ml. The resultant slurry was cooled to 5° C. and granulated for 1 hour, then collected by filtration to yield the title compound as a white solid (135.2 g, 65%).

$^1$H-NMR (300 MHz, CDCl$_3$): δ=2.98-3.01 (t, 2H), 3.68-3.72 (t, 2H), 7.37-7.40 (d, 1H), 7.48-7.63 (m, 3H), 7.76 (s, 1H), 7.78 (s, 1H), 7.95 (s, 1H).

Example 7

Preparation of 6-bromo-3-(2-{[2-(triisopropylsiloxy)ethyl]sulfanyl}phenyl)[1,2,4]triazolo[4,3-a]pyridine

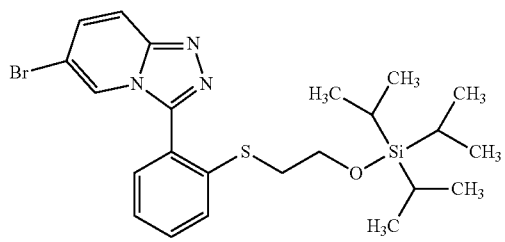

To a slurry of alcohol of Example 6 (51.3 g, 0.146 moles) in 2-methyltetrahydrofuran (257 ml) was added imidazole (11.9 g, 0.175 moles) and dimethylaminopyridine (1.79 g, 0.015 moles). Chlorotriisopropylsilane (33.9 g, 0.175 moles) was added over 10 minutes and the resultant mixture heated at 50° C. for 18 hours. The reaction was cooled to 20° C. and washed with 1M hydrochloric acid solution (257 ml) and the aqueous extracted with 2-methyltetrahydrofuran (103 ml). The combined organics were washed with 10% w/w sodium chloride solution, then distilled under reduced pressure, and replaced with n-heptane to give a final volume of 513 ml. The resultant slurry was cooled to 5° C. and granulated for 18 hours. The solid was collected by filtration to give the title compound as a white solid (63.0 g, 87%).

$^1$H-NMR (300 MHz, CDCl$_3$): δ=0.99-1.08 (m, 21H), 2.97-3.01 (t, 2H), 3.76-3.81 (t, 2H), 7.35-7.44 (m, 2H), 7.30-7.36 (m, 2H), 7.65-7.68 (d, 1H), 7.75-7.79 (d, 1H), 7.90 (s, 1H).

Example 8

Preparation of [2-({3-[2-({2-[(triisopropylsilyl)oxy]ethyl}sulfanyl) phenyl][1,2,4]triazolo[4,3-a]pyridin-6-yl}sulfanyl)phenyl]methanol

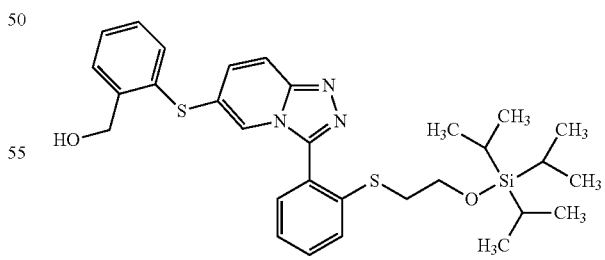

To a solution of aryl bromide of Example 7 (50.7 g, 0.10 moles) in toluene (250 ml) was added (2-sulfanylphenyl)methanol (16.8 g, 0.12 moles), sodium (tert)-butoxide (14.4 g, 015 moles) and [1,1'-bis(diphenylphosphino)ferrocene] dichloro palladium (II) (0.41 g, 0.0005 moles). The resultant mixture was sparged with nitrogen for 10 minutes then heated at 111° C. for 16 hours. The reaction was cooled to 20° C., diluted with isopropyl acetate (200 ml) and washed with 2M hydrochloric acid solution (250 ml). The aqueous phase was extracted with isopropyl acetate (50 ml) and the combined organics were washed sequentially with 1M sodium hydroxide solution (250 ml) and 10% w/w sodium chloride solution (250 ml). The solvent was distilled under reduced pressure and replaced with (tert)-butyl methyl ether to give a final volume of 250 ml. The solution was cooled to 5° C. and granulated for 5 hours, then solid was collected by filtration to give the title compound as a white solid (38.5 g, 68%).

$^1$H-NMR (300 MHz, CDCl$_3$): δ=0.99-1.05 (m, 21H), 2.93-2.98 (t, 2H), 3.74-3.79 (t, 2H), 4.86 (s, 2H), 7.13-7.26 (d, $^1$H-NMR (300 MHz, d6-DMSO): δ=0.88-0.99 (m, 21H), 3.05-3.07 (t, 2H), 3.73-3.77 (t, 2H), 3.85 (s, 2H), 7.14-7.29 (m, H).

Example 10

Preparation of N-{3-tert-butyl-1-[3-chloro-4-(triisopropylsiloxy) phenyl]-1H-pyrazol-5-yl}-N'-(2-{[3-(2-{[2-(triisopropylsiloxy)ethyl]sulfanyl}phenyl) [1,2,4]triazolo[4,3-a]pyridin-6-yl]sulfanyl}benzyl) urea

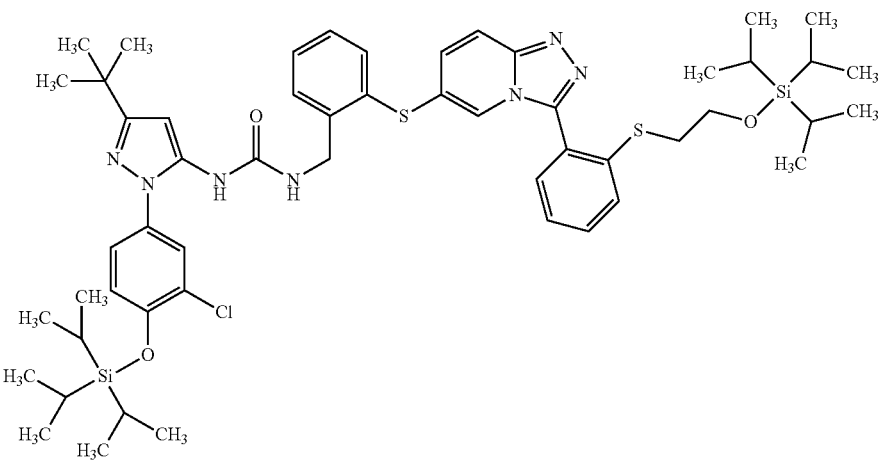

1H), 7.25-7.28 (m, 2H), 7.31-7.38 (m, 1H), 7.40-7.43 (d, 1H), 7.51-7.60 (m, 3H), 7.63-7.65 (d, 1H), 7.74-7.77 (m, 2H).

Example 9

Preparation of 1-[2-({3-[2-({2-[(triisopropylsilyl)oxy]ethyl}sulfanyl)phenyl][1,2,4]triazolo[4,3-a]pyridin-6-yl}sulfanyl)phenyl]methanamine

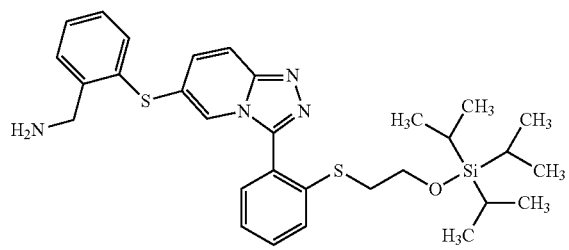

To a slurry of benzyl alcohol of Example 8 (25.0 g, 0.044 moles) in toluene (250 ml), was added methanesulfonic anhydride (10.77 g, 0.062 moles) then cooled to 5° C. Triethylamine (6.93 g, 0.068 moles) was added over 30 minutes and stirred at this temperature for 3 hours. The resultant solution was added to 7M ammonia in methanol solution (316 ml, 2.21 moles) and stirred for 16 hours. Water (250 ml) was added and the organic phase washed with water (250 ml). The aqueous phases were extracted with toluene (125 ml) and the combined organics were dried by azeotropic distillation under reduced pressure to leave the title compound as a clear brown solution in toluene (125 ml) (assumed quantitative yield).

To a solution of benzylamine of Example 9 (30.0 g, 0.053 moles) in toluene (300 ml) was added the phenyl carbamate of Example 3 (27.3 g, 0.50 moles) and diisopropylethylamine (7.31 g, 0.058 moles) and stirred for 3 hours. Ethyl acetate (150 ml) was added and washed sequentially with 1M sodium hydroxide solution (300 ml) and water (300 ml). The solution was dried by azeotropic distillation under reduced pressure and solvent replaced with methanol to leave the title compound as a clear brown solution in methanol (275 ml) (assumed quantitative yield). The material was used directly in the subsequent step without isolation or purification.

Example 11

Preparation of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea (polymorph A)

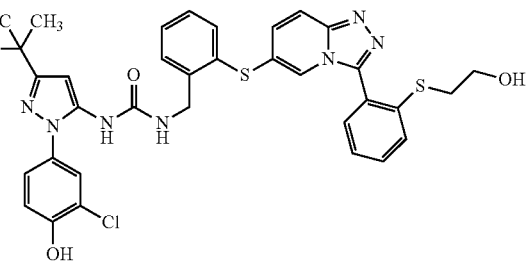

A solution of urea of Example 10 (71.6 g, 0.707 moles) in methanol (360 ml) was heated to 50° C. and 2M hydrochloric acid (360 ml) was added over 75 minutes. The resultant solution was heated at 65° C. for 4 hours then cooled to 20° C. Dichloromethane (430 ml) and water (215 ml) were added and the aqueous was extracted with dichloromethane (2×215 ml). To the combined organics was added methanol (35 ml) and washed with water (215 ml). The organics were distilled under reduced pressure and replaced with fresh methanol to give a final solution of 215 ml. The resultant solution was cooled to −5° C. for 16 hours and the solid collected by filtration to give the title compound (polymorph A) as a white solid (27.3 g, 55%).
Polymorph A Identified by PXRD.

$^1$H-NMR (300 MHz, d6-DMSO): δ=1.24 (s, 9H), 2.96-3.01 (t, 2H), 3.47-3.51 (t, 2H), 4.36-4.38 (d, 2H), 4.89 (br s, 1H), 6.21 (s, 1H), 6.93-6.97 (t, 1H), 7.03-7.06 (d, 1H), 7.21-7.42 (m, 6H), 7.55-7.67 (m, 3H), 7.86-7.93 (m, 2H), 8.20 (s, 1H).

Example 12

Preparation of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea (polymorph B)

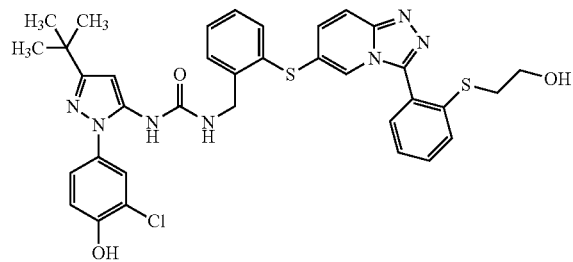

A slurry of polymorph A of Example 10 (15.0 g, 0.0214 moles) in methanol (450 ml) was heated at 65° C. for 5 hours. Methanol was removed by distillation to give a volume of 225 ml, at which point a seed of polymorph B was added. Heating at 65° C. was continued at this volume for a further 16 hours. The volume was further reduced by distillation of methanol to 75 ml, cooled to −5° C. and granulated at this temperature for 3 hours. The solid was collected by filtration to give the title compound (polymorph B) as a white solid (13.5 g, 90%).
Polymorph B Identified by PXRD $^1$H-NMR (300 MHz, d6-DMSO): δ=1.24 (s, 9H), 2.96-3.01 (t, 2H), 3.47-3.51 (t, 2H), 4.36-4.38 (d, 2H), 4.89 (br s, 1H), 6.21 (s, 1H), 6.93-6.97 (t, 1H), 7.03-7.06 (d, 1H), 7.21-7.42 (m, 6H), 7.55-7.67 (m, 3H), 7.86-7.93 (m, 2H), 8.20 (s, 1H).
Characterisation
(a) Powder X-Ray Diffraction (PXRD)

Powder X-ray diffraction patterns were determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha$_1$ X-rays (wavelength=1.5406 Ångstroms) with the X-ray tube operated at 40 kV/30 mA. The analyses were performed with the goniometer running in continuous mode set for a 0.2 second count per 0.018° step over a two theta range of 2° to 55°. Peaks were selected manually using Bruker-AXS Ltd. evaluation software.

As will be appreciated by the skilled person, the relative intensities of the various peaks given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined.

The skilled person will also appreciate that measurements using a different wavelength will result in different shifts according to the Bragg equation—$n\lambda=2d \sin \theta$, Such further PXRD patterns generated by use of alternative wavelengths are considered to be alternative representations of the PXRD patterns of the crystalline materials of the present invention and as such are within the scope of the present invention.

For calculated PXRD patterns, 2θ angles and relative intensities were calculated from the single crystal structure using the "Reflex Powder Diffraction" module of Accelrys MS Modelling™ [version 3.0]. Pertinent simulation parameters were:
Wavelength=1.5406 Å (Cu Kα)
Polarisation Factor=0.5
Pseudo-Voigt Profile (U=0.01, V=−0.001, W=0.002).

The PXRD pattern for Form A is shown in FIG. 1. The main peaks (greater than 10% relative intensity) are listed below in Table 1. Form A displays characteristic diffraction peaks at 6.7, 7.4, 9.5, 12.2 and 14.9 degrees two theta (±0.1 degrees).

TABLE 1

Main PXRD peaks for Form A

| 2-Theta (°) | Intensity (%) |
|---|---|
| 6.7 | 69.1 |
| 7.4 | 55.8 |
| 7.5 | 33.2 |
| 9.4 | 31.3 |
| 9.5 | 62.2 |
| 11.4 | 42.0 |
| 12.2 | 59.5 |
| 14.9 | 61.7 |
| 15.5 | 39.3 |
| 16.6 | 25.9 |
| 17.2 | 32.6 |
| 17.8 | 31.6 |
| 18.2 | 24.6 |
| 18.3 | 24.3 |
| 18.9 | 65.6 |
| 19.1 | 40.4 |
| 19.9 | 39.4 |
| 20.1 | 51.9 |
| 20.5 | 62.7 |
| 21.1 | 60.3 |
| 21.9 | 37.4 |
| 22.1 | 40.6 |
| 22.4 | 39.5 |
| 22.8 | 100.0 |
| 23.8 | 31.5 |
| 24.0 | 45.5 |
| 24.3 | 34.6 |
| 24.4 | 33.8 |
| 25.1 | 26.0 |
| 25.7 | 30.4 |
| 26.9 | 30.4 |
| 27.5 | 49.6 |
| 28.3 | 25.6 |
| 28.7 | 28.1 |
| 29.3 | 33.4 |
| 29.9 | 27.2 |
| 30.1 | 23.9 |

TABLE 1-continued

| Main PXRD peaks for Form A | |
|---|---|
| 2-Theta (°) | Intensity (%) |
| 31.2 | 24.3 |
| 32.2 | 28.0 |
| 34.7 | 24.0 |
| 34.9 | 30.6 |
| 38.3 | 24.7 |

Figure 2:
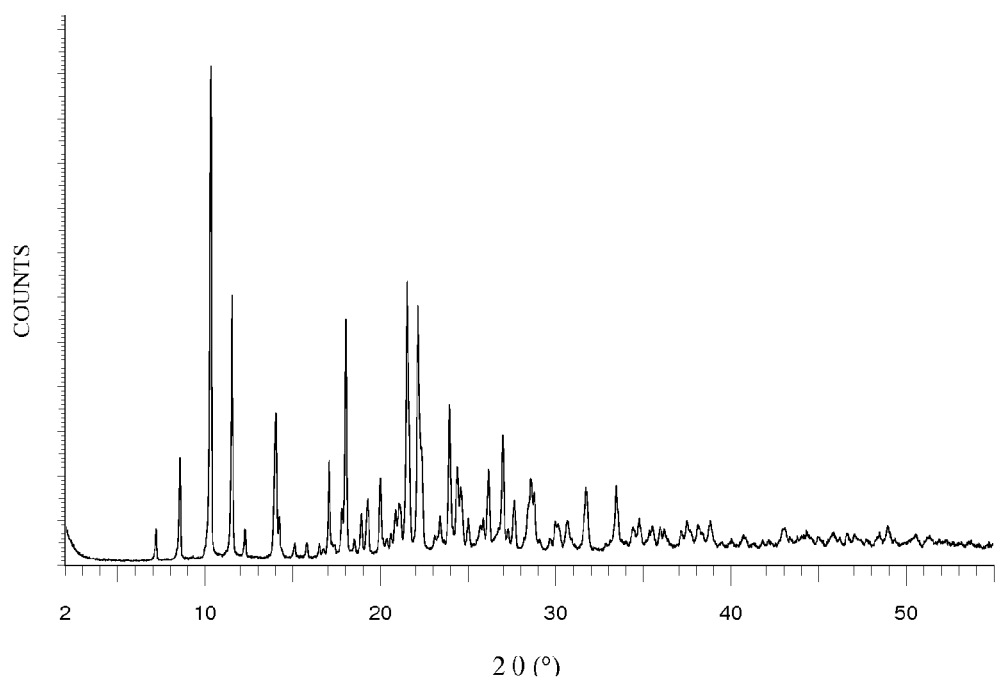
FIG. 2 shows an illustrative PXRD pattern for Form B.

The PXRD pattern for Form B is shown in FIG. 2. The main peaks (greater than 10% relative intensity) are listed below in Table 2. Form B displays characteristic diffraction peaks at 8.5, 10.3, 11.5, 14.0 and 21.5 degrees two theta (±0.1 degrees).

TABLE 2

| Main PXRD peaks for Form B | |
|---|---|
| 2-Theta (°) | Intensity (%) |
| 8.5 | 21.4 |
| 10.3 | 100.0 |
| 11.5 | 54.1 |
| 14.0 | 30.1 |
| 17.0 | 20.9 |
| 17.8 | 11.2 |
| 18.0 | 49.1 |
| 18.9 | 10.1 |
| 19.2 | 13.1 |
| 20.0 | 17.2 |
| 20.8 | 11.0 |
| 21.1 | 12.0 |
| 21.5 | 56.8 |
| 22.1 | 51.9 |
| 22.3 | 23.6 |
| 23.4 | 9.6 |
| 23.9 | 32.0 |
| 24.4 | 19.6 |
| 24.6 | 15.5 |
| 25.0 | 9.2 |
| 25.8 | 9.4 |
| 26.2 | 19.0 |
| 27.0 | 25.9 |
| 27.6 | 12.9 |
| 28.4 | 11.2 |
| 28.6 | 17.2 |
| 28.7 | 14.4 |
| 31.7 | 15.4 |
| 33.5 | 15.7 |
| 34.8 | 9.2 |

(b) Differential Scanning Calorimetry (DSC)

Samples were heated from 20 to 300° C. at 10° C. per minute using a TA Instruments Q1000 DSC with vented aluminium pan and lid. Nitrogen was used as purge gas.

Figure 3:
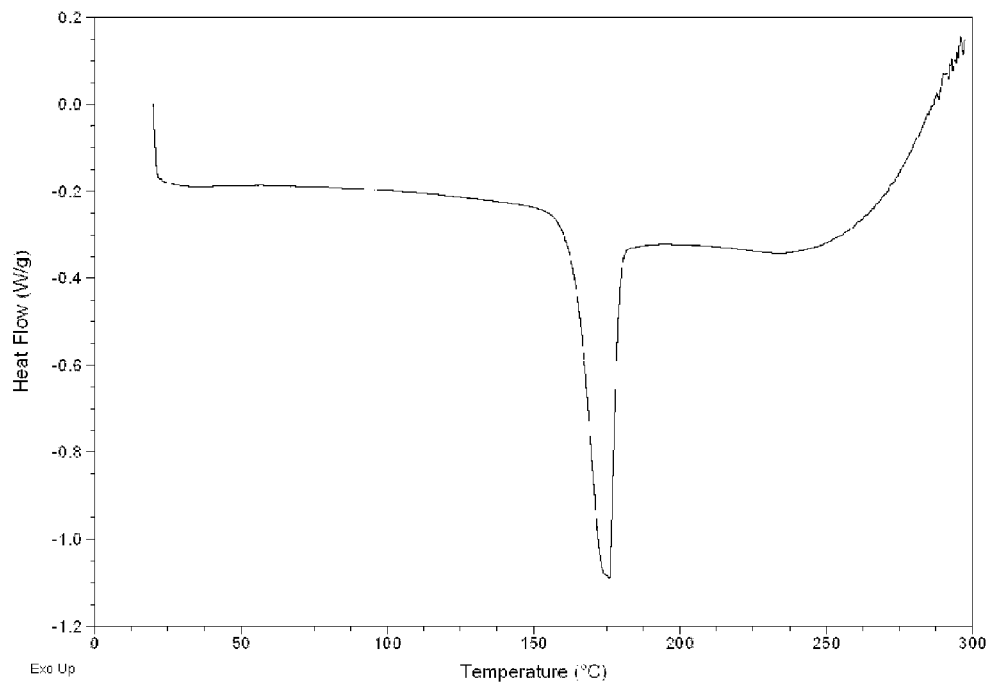
FIG. 3 shows an illustrative DSC thermogram for Form A.

The DSC thermogram for PF-03715455 Form A is shown in FIG. 3. A sharp endotherm is observed with an onset temperature of 164° C. and a peak maximum at 174° C.

Figure 4:
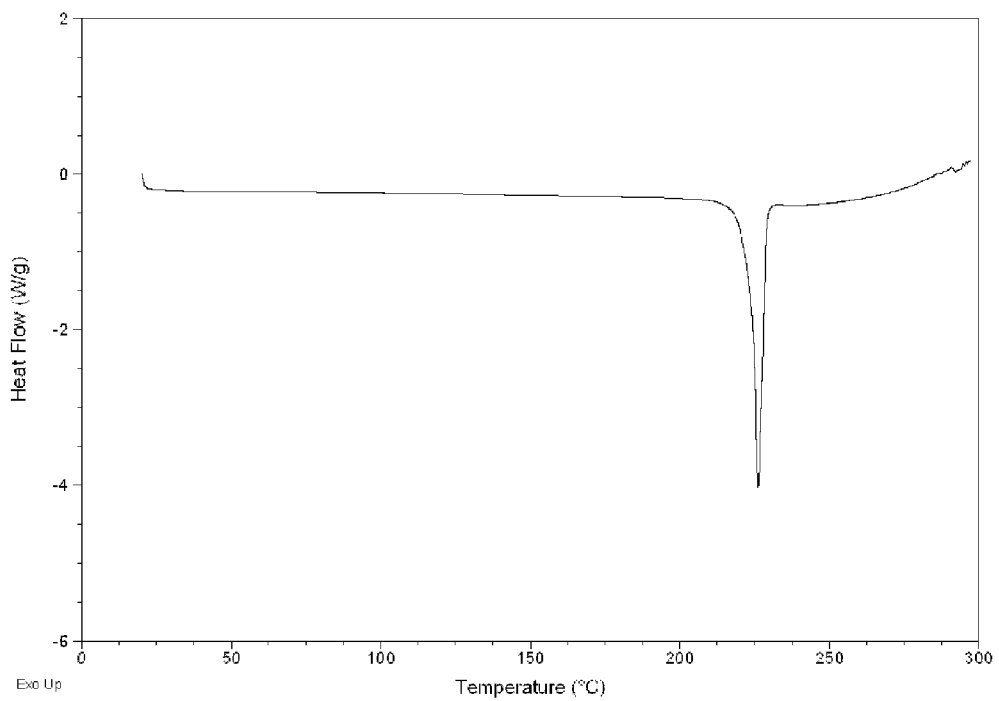
FIG. 4 shows an illustrative DSC thermogram for Form B.

The DSC thermogram for PF-03715455 Form B is shown in FIG. 4. A sharp endotherm is observed with an onset temperature of 224° C. and a peak maximum at 226° C.

(c) Thermogravimetric Analysis (TGA)

Mass loss on drying was measured using TA Instruments Thermogravimetric analyser TGA2950 Hi-Res with nitrogen purge gas. Samples were heated from ambient to 300° C. at a heating rate of 10° C./min.

Figure 5:
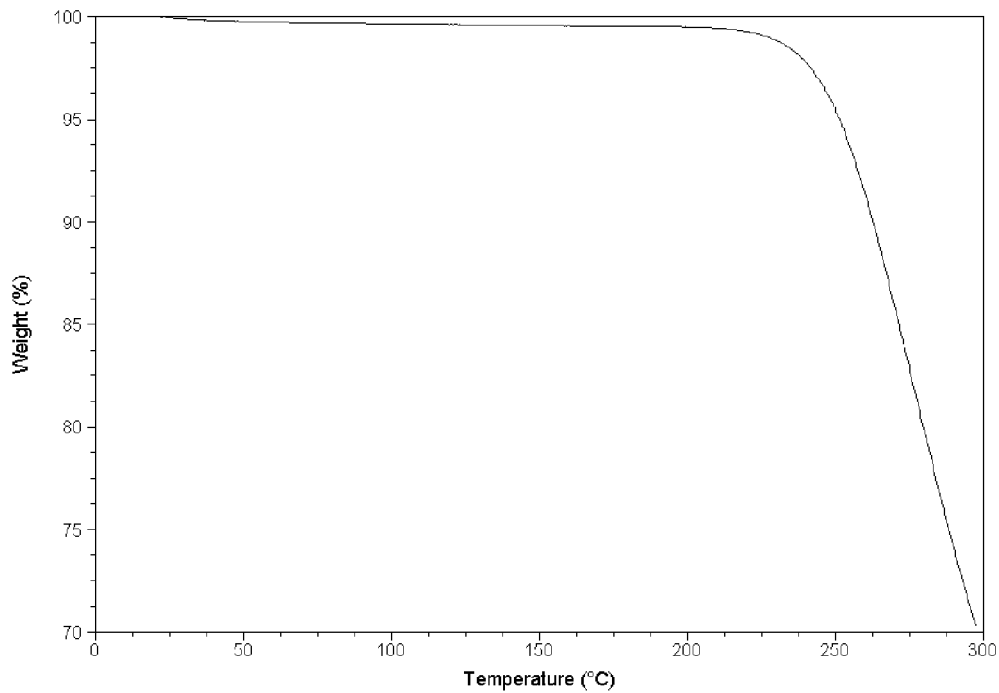
FIG. 5 shows an illustrative mass loss curve obtained from thermogravimetric analysis of Form A.

The mass loss curve obtained from thermogravimetric analysis of Form A is shown in FIG. 5. On heating from ambient to 150° C. a mass loss of 0.41% was observed.

Figure 6:
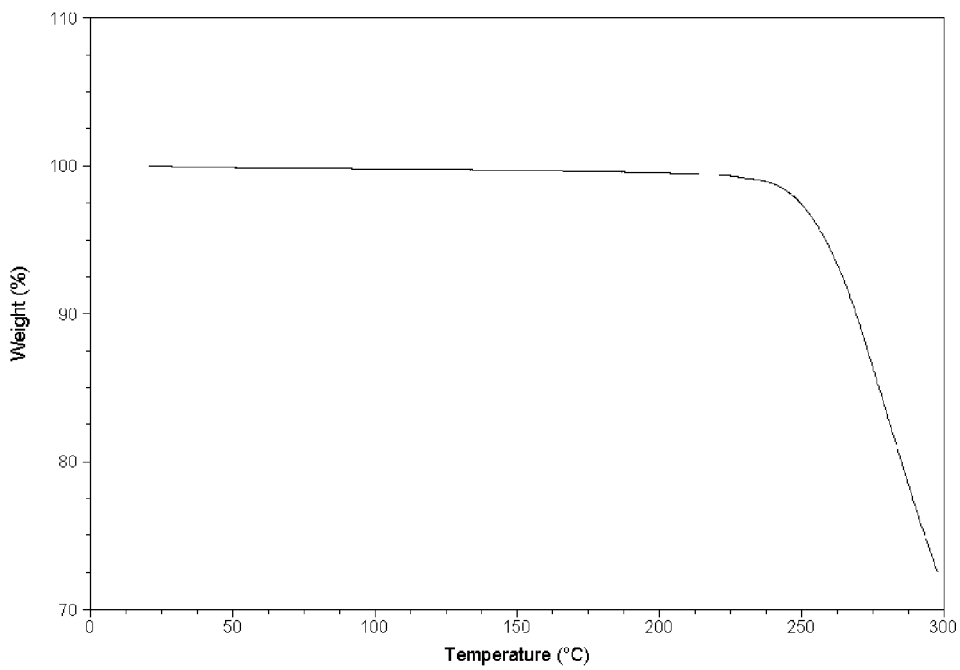
FIG. 6 shows an illustrative mass loss curve obtained from thermogravimetric analysis of Form B.

The mass loss curve obtained from thermogravimetric analysis of Form B is shown in FIG. 6. On heating from ambient to 150° C. a mass loss of 0.30% was observed.

(d) Fourier Transform Infra Red Analysis (FT-IR)

FT-IR spectra were acquired using a ThermoNicolet Nexus FTIR spectrometer equipped with a 'DurasamplIR' single reflection ATR accessory (diamond surface on zinc selenide substrate) and d-TGS KBr detector. The spectrum was collected at 2 cm$^{-1}$ resolution and a co-addition of 256 scans for all compounds. Happ-Genzel apodization was used. Because the FT-IR spectrum was recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$.

Peaks were picked using ThermoNicolet Omnic 6.0a software. Intensity assignments are relative to the major band in the spectrum and are therefore not based on absolute values measured from the baseline.

Figure 7:
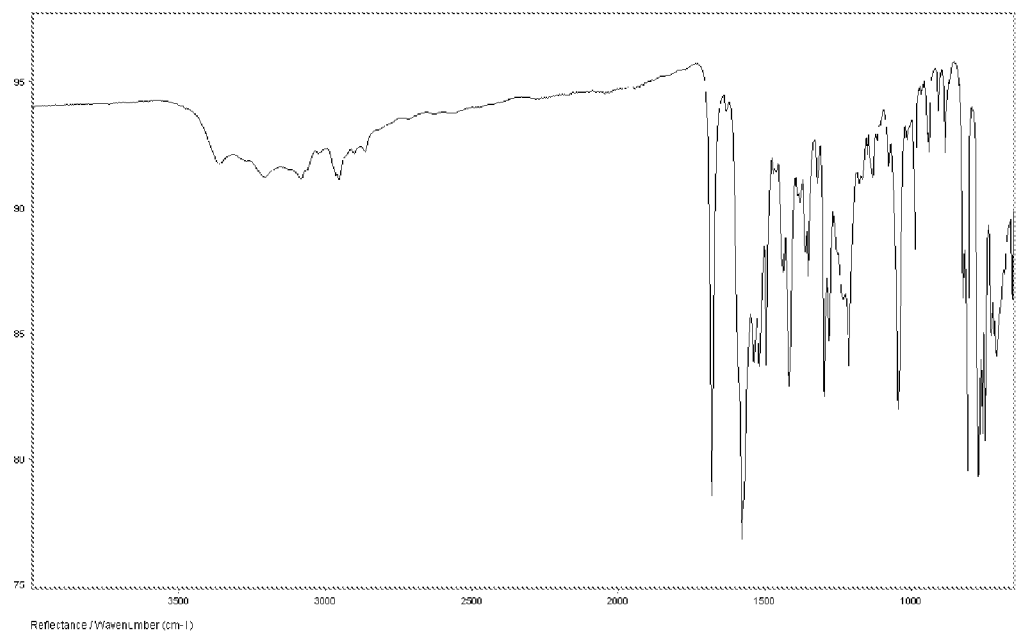
FIG. 7 shows an illustrative FT-IR spectrum for Form A.
Figure 7:
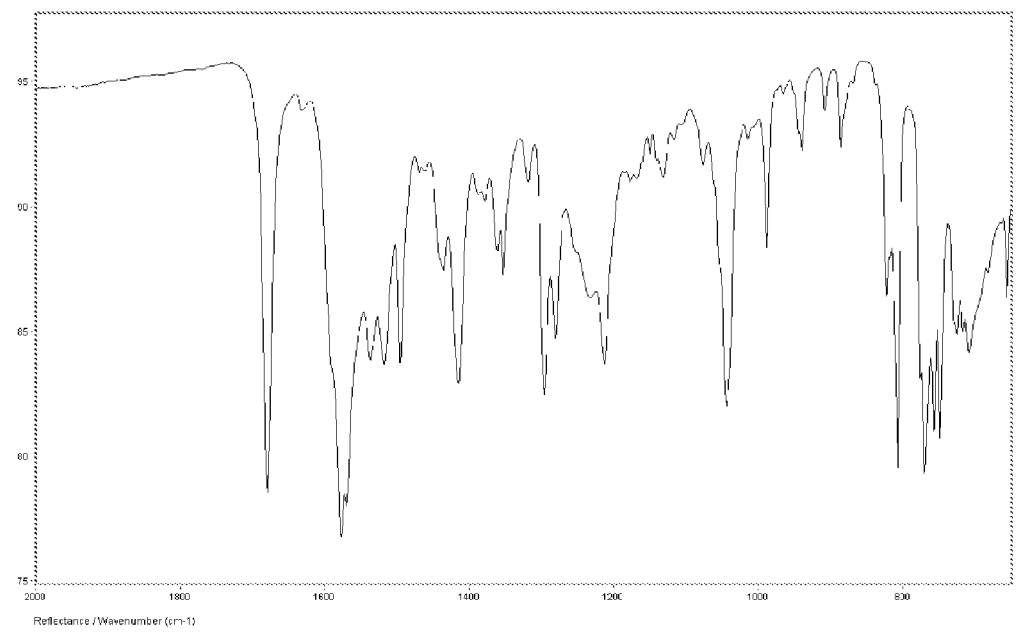

The FT-IR spectrum for Form A is illustrated in FIG. 7. The main peaks are listed below in Table 3 (w=weak, m=medium, s=strong; experimental error is ±2 cm$^{-1}$ except for peaks marked * where error on peak position could be considerably larger). Form A displays characteristic absorption bands at 769, 806, 1211, 1295 and 1517 cm$^{-1}$.

TABLE 3

| FT-IR peaks for Form A | | | |
|---|---|---|---|
| Wavenumber (cm$^{-1}$) | Wavenumber (cm$^{-1}$) | Wavenumber (cm$^{-1}$) | Wavenumber (cm$^{-1}$) |
| 3363 m* | 1536 m | 1280 m | 806 s |
| 3204 m* | 1517 m | 1211 s | 769 s |
| 3083 m | 1495 m | 1130 w | 756 m |
| 2951 m | 1435 w | 1043 s | 747 m |
| 2899 w | 1414 s | 987 m | 724 m |
| 2863 w | 1360 w | 939 w | 716 w |
| 1679 s | 1352 w | 907 w | 708 m |
| 1577 s | 1317 w | 885 w | 655 m |
| 1569 m | 1295 s | 821 w | |

Figure 8:
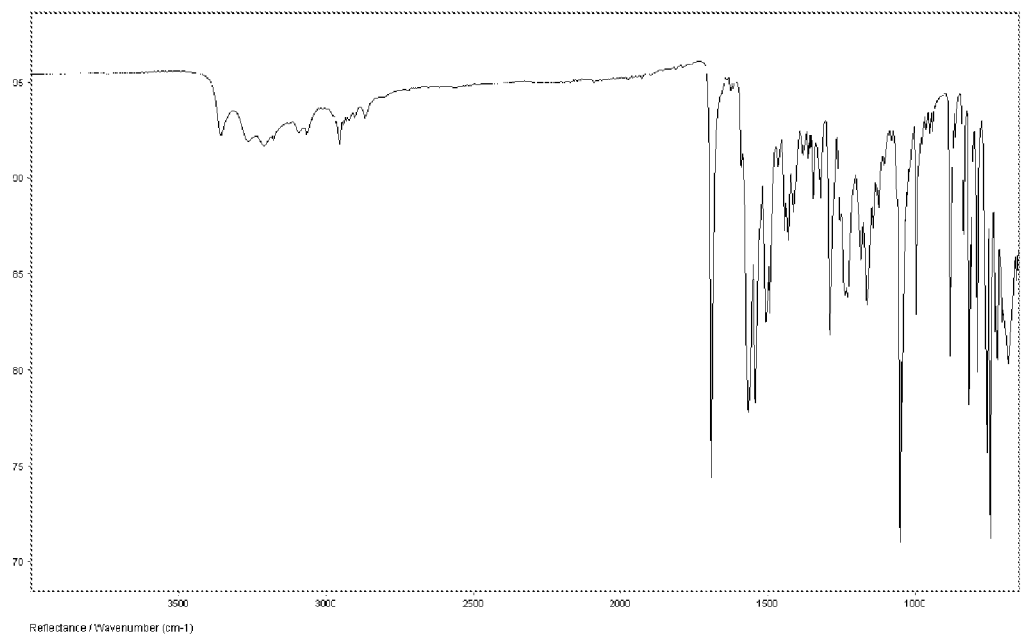
FIG. 8 shows an illustrative FT-IR spectrum for Form B.
Figure 8:
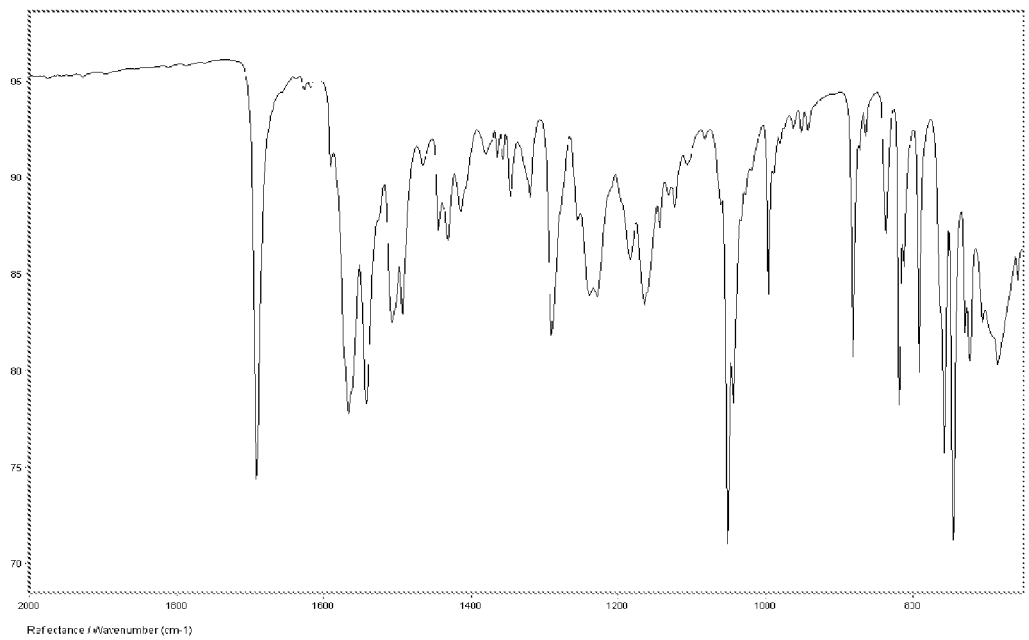

The FT-IR spectrum for Form B is illustrated in FIG. 8. The main peaks are listed below in Table 4 (w=weak, m=medium, s=strong; experimental error is ±2 cm$^{-1}$ except for peaks marked * where error on peak position could be considerably larger). Form B displays characteristic absorption bands at 790, 880, 995, 1507 and 1542 cm$^{-1}$.

TABLE 4

| FT-IR peaks for Form B | | | |
|---|---|---|---|
| Wavenumber (cm$^{-1}$) | Wavenumber (cm$^{-1}$) | Wavenumber (cm$^{-1}$) | Wavenumber (cm$^{-1}$) |
| 3355 w* | 1507 m | 1228 m | 818 s |
| 3263 w* | 1493 m | 1183 w | 811 w |
| 3210 w* | 1444 w | 1164 m | 790 s |
| 3063 w | 1431 m | 1143 w | 756 s |
| 2953 w | 1413 m | 1051 s | 744 s |
| 2866 w | 1345 m | 1043 m | 728 w |
| 1691 s | 1319 m | 995 s | 721 m |
| 1566 s | 1290 s | 880 s | 684 m |
| 1542 s | 1238 m | 835 m | 657 w |

(e) Fourier Transform Raman Analysis (FT-Raman)

Raman spectra were collected using a Bruker Vertex70 with RamII module FT-Raman spectrometer equipped with a 1064 nm NdYAG laser and LN-Germanium detector. The spectrum was recorded using 2 cm$^{-1}$ resolution and Blackman-Harris 4-term apodization. Laser power was 300 mW and 4096 co-added scans were collected except for the amorphous sample where laser power was 400 mW. Each sample was placed in a glass vial and exposed to the laser radiation. The data is presented as intensity as a function of Raman shift and is corrected for instrument response and frequency dependent scattering using a white light spectrum from a reference lamp. The Bruker Raman Correct function was used to do the correction. (Bruker software—OPUS 6.0). Experimental error, unless otherwise noted, was ±2 cm$^{-1}$.

Peaks were picked using ThermoNicolet Omnic 6.0a software. Intensity assignments are relative to the major band in the spectrum and are therefore not based on absolute values measured from the baseline.

Figure 9:
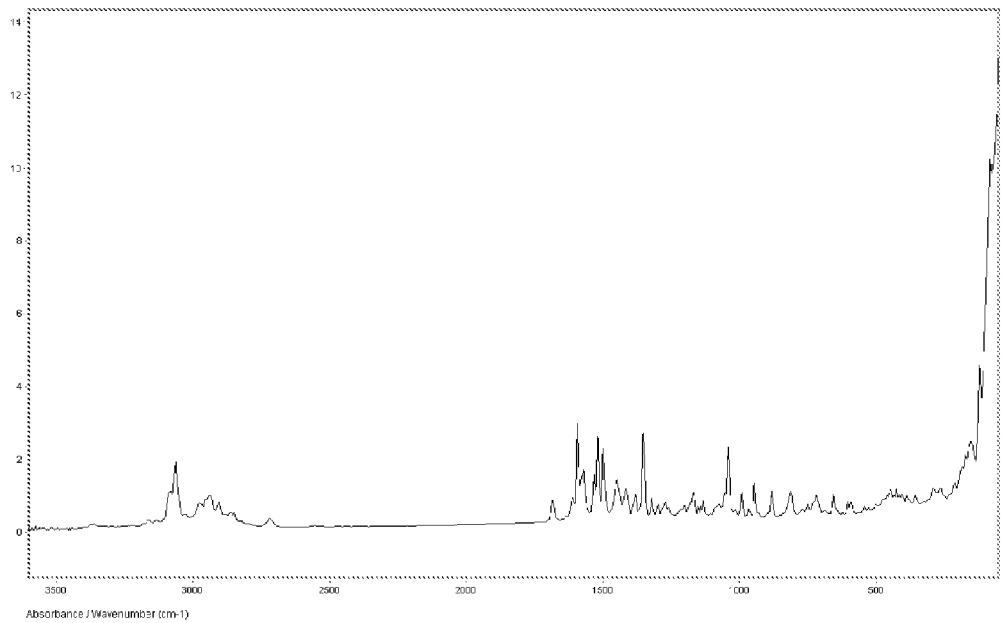
FIG. 9 shows an illustrative FT-Raman spectrum for Form A.
Figure 9:
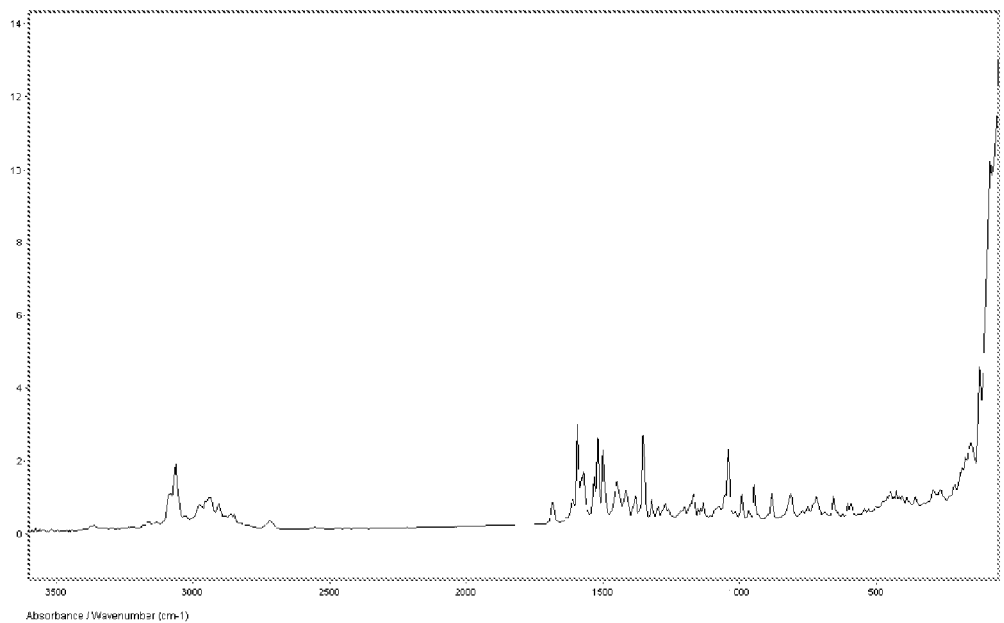

The FT-Raman spectrum for Form A is illustrated in FIG. 9. The main peaks are listed below in Table 5 (w=weak, m=medium, s=strong, vs=very strong; experimental error is ±2 cm$^{-1}$ except for peaks marked ** where error is ±1 cm$^{-1}$). Form A displays characteristic absorption bands at 81, 122, 290, 1039 and 1518 cm$^{-1}$.

TABLE 5

FT-Raman peaks for Form A

| Wavenumber (cm$^{-1}$) | Wavenumber (cm$^{-1}$) | Wavenumber (cm$^{-1}$) | Wavenumber (cm$^{-1}$) |
|---|---|---|---|
| 3160 w | 1533 m | 1131 m | 447 m |
| 3081 m | 1518 s | 1039 s | 426 m |
| 3063 s | 1497 s | 989 m | 404 m |
| 3028 w | 1447 m | 965 w | 388 m |
| 2976 w | 1414 m | 945 m | 355 m |
| 2937 m | 1379 m | 881 m | 290 m |
| 2903 m | 1353 s | 810 m | 264 m |
| 2860 w | 1319 m | 749 w | 211 m |
| 2848 w | 1298 w | 718 m | 173 s |
| 2718 w | 1271 m | 656 m | 152 s |
| 1682 m | 1201 w | 601 m | 122 vs** |
| 1609 w | 1167 m | 591 m | 81 vs** |
| 1592 s | 1151 w | 542 w | |
| 1570 m | 1142 w | 528 w | |

Figure 10:
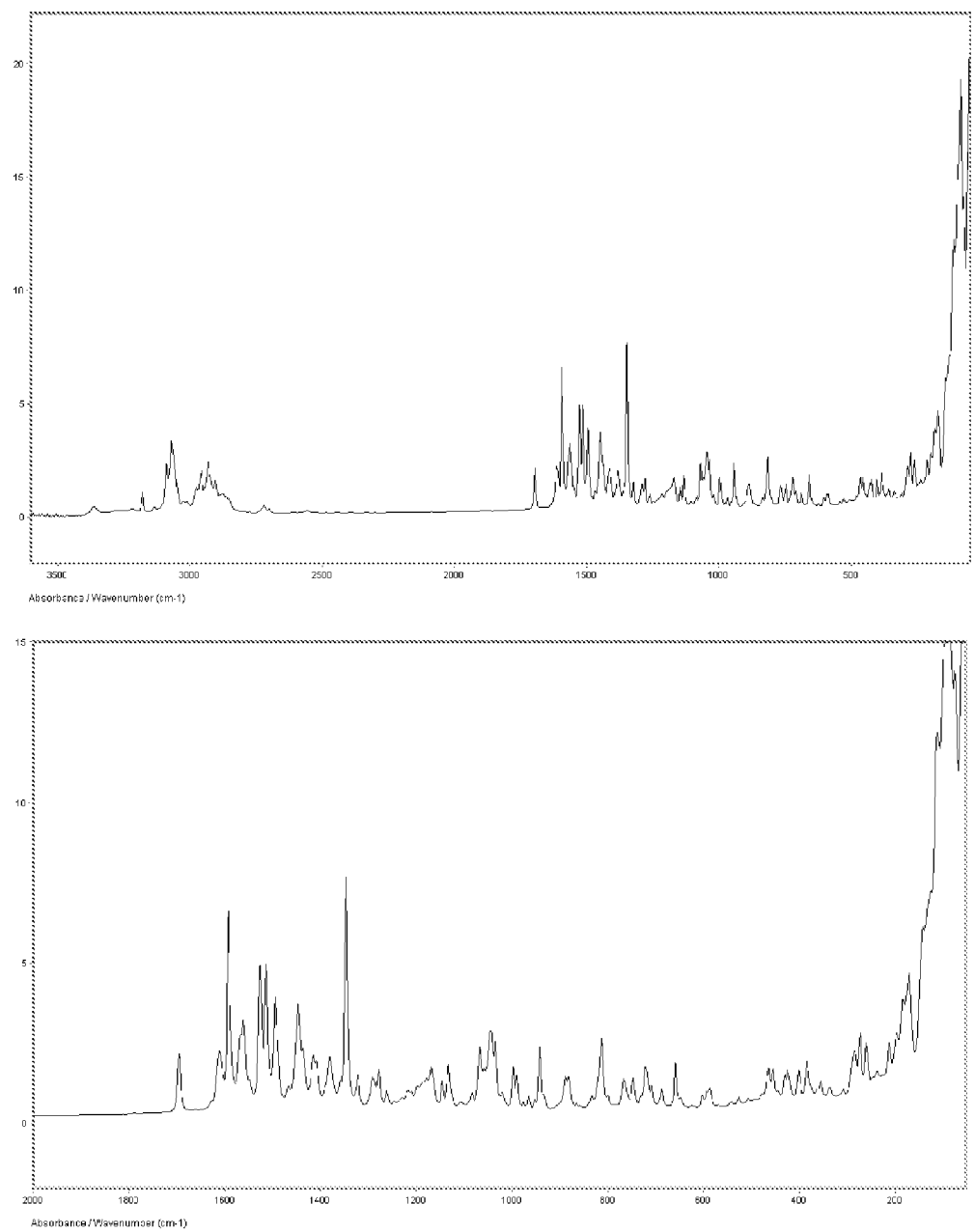
FIG. 10 shows an illustrative FT-Raman spectrum for Form B.

The FT-Raman spectrum for Form B is illustrated in FIG. 10. The main peaks are listed below in Table 6 (w=weak, m=medium, s=strong, vs=very strong; experimental error is ±2 cm$^{-1}$ except for peaks marked * where error could be considerably larger and peaks marked ** where error is ±1 cm$^{-1}$). Form B displays characteristic absorption bands at 85, 111, 272, 997 and 1513 cm$^{-1}$.

TABLE 6

FT-Raman peaks for Form B

| Wavenumber (cm$^{-1}$) | Wavenumber (cm$^{-1}$) | Wavenumber (cm$^{-1}$) | Wavenumber (cm$^{-1}$) |
|---|---|---|---|
| 3361 w* | 1513 s | 997 w | 383 w |
| 3178 w | 1494 m | 989 w | 354 w |
| 3087 m | 1446 m | 942 m | 335 w |
| 3069 m | 1414 m | 887 w | 283 w |
| 3046 w | 1379 m | 881 w | 272 m |
| 2975 w | 1346 s | 812 m | 259 w |
| 2956 m | 1321 w | 746 w | 211 w |
| 2930 m | 1290 w | 720 w | 195 w |
| 2902 w | 1277 w | 686 w | 182 w |

TABLE 6-continued

FT-Raman peaks for Form B

| Wavenumber (cm$^{-1}$) | Wavenumber (cm$^{-1}$) | Wavenumber (cm$^{-1}$) | Wavenumber (cm$^{-1}$) |
|---|---|---|---|
| 2719 w | 1168 w | 586 w | 169 m |
| 1694 m | 1145 w | 463 w | 111 s |
| 1610 m | 1132 w | 454 w | 97 m |
| 1592 s | 1067 m | 429 w | 85 vs |
| 1560 m | 1044 m | 423 w | 74 m |
| 1525 s | 1034 m | 401 w | 59 s |

(f) Solid State $^{13}$C Nuclear Magnetic Resonance (SSNMR)

Approximately 80 mg of each sample was tightly packed into a 4 mm ZrO$_2$ spinner. The spectra were collected at ambient conditions on a Bruker-Biospin 4 mm BL HFX CPMAS probe positioned into a wide-bore Bruker-Biospin Avance DSX 500 MHz NMR spectrometer. The spinner was positioned at the magic angle and spun at 15.0 kHz. The fast spinning speed minimized the intensities of the spinning side bands. The number of scans was adjusted to obtain an adequate signal to noise ratio. The $^{13}$C solid state spectrum was collected using a proton decoupled cross-polarization magic angle spinning experiment (CPMAS). A proton decoupling field of approximately 90 kHz was applied. The spectra were referenced using an external standard of crystalline adamantane, setting its upfield resonance to 29.5 ppm.

Figure 11:
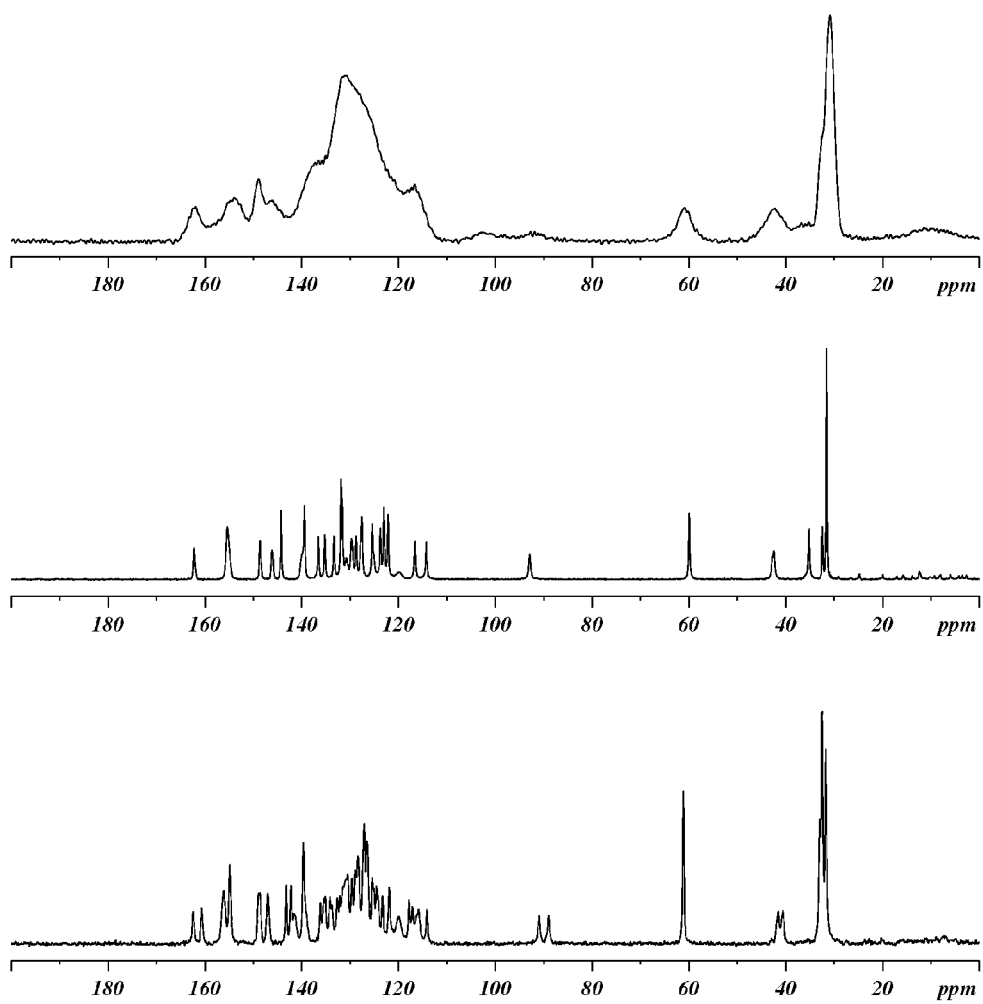
FIG. 11 shows an illustrative $^{13}$C SSNMR spectrum for Form A, Form B and amorphous material, where the amorphous is the top, Form B is in the middle and Form A is at the bottom.

The $^{13}$C SSNMR spectrum for Form A, Form B and amorphous material are shown FIG. 11 (amorphous at the top, Form B in the middle and Form A at the bottom). The corresponding peaks are listed below in Tables 7-9 below. Intensity is defined as peak height which an vary depending on the actual setup of the CPMAS experimental parameters and the thermal history of the sample. CPMAS intensities are not necessarily quantitative.

TABLE 7

$^{13}$C SSNMR data for Form A

| Chemical Shift [ppm] | Intensity |
|---|---|
| 162.5 | 1.53 |
| 160.7 | 1.71 |
| 156.1 | 2.63 |
| 154.9 | 4 |
| 148.9 | 2.48 |
| 148.6 | 2.5 |
| 147.0 | 2.48 |
| 143.2 | 2.92 |
| 142.2 | 2.86 |
| 141.6 | 1.43 |
| 141.3 shoulder | — |
| 141.0 shoulder | — |
| 139.7 | 5.12 |
| 139.1 shoulder | — |
| 138.8 shoulder | — |
| 136.1 | 1.98 |
| 135.5 | 2.2 |
| 135.1 | 2.34 |
| 134.2 | 2.29 |
| 133.8 | 1.88 |
| 132.7 | 2.24 |
| 132.1 | 2.38 |
| 131.5 shoulder | — |
| 130.9 shoulder | — |

TABLE 7-continued

$^{13}$C SSNMR data for Form A

| Chemical Shift [ppm] | Intensity |
|---|---|
| 130.5 | 3.46 |
| 129.7 | 3.27 |
| 128.9 | 3.69 |
| 128.4 | 4.44 |
| 127.1 | 6.1 |
| 126.5 | 5.22 |
| 125.4 | 3.32 |
| 125.1 | 2.75 |
| 124.6 | 2.85 |
| 124.2 | 2.36 |
| 123.3 | 2.36 |
| 121.9 | 2.79 |
| 120.0 | 1.27 |
| 117.9 | 2.14 |
| 117.1 | 1.79 |
| 116.3 shoulder | — |
| 115.9 | 1.65 |
| 114.1 | 1.62 |
| 91.0 | 1.29 |
| 89.0 | 1.33 |
| 61.2 | 7.85 |
| 41.9 shoulder | — |
| 41.6 | 1.54 |
| 40.8 shoulder | — |
| 40.6 | 1.56 |
| 33.0 | 6.37 |
| 32.5 | 12 |
| 31.7 | 10.03 |

Form A displays characteristic chemical shifts at 160.7, 147.0, 143.2, 127.1, 117.9, 40.6 and 33.0 ppm.

TABLE 8

$^{13}$C SSNMR data for Form B

| Chemical Shift [ppm] | Intensity |
|---|---|
| 162.3 | 1.56 |
| 155.4 | 2.66 |
| 148.6 | 1.96 |
| 146.2 | 1.44 |
| 144.3 | 3.51 |
| 140.0 shoulder | — |
| 139.4 | 3.75 |
| 136.6 | 2.15 |
| 135.2 | 2.25 |
| 133.4 | 2.17 |
| 131.9 | 5.17 |
| 131.7 | 4.11 |
| 130.8 | 1.05 |
| 129.7 | 2.04 |
| 128.8 | 2.17 |
| 127.7 shoulder | — |
| 127.6 | 3.17 |
| 125.4 | 2.8 |
| 125.1 shoulder | — |
| 123.8 | 2.61 |
| 123.0 | 3.67 |
| 122.2 | 3.31 |
| 120.0 | 0.31 |
| 116.6 | 1.93 |
| 114.3 | 1.85 |
| 92.9 | 1.22 |
| 60.0 | 3.37 |
| 42.7 | — |

TABLE 8-continued

$^{13}$C SSNMR data for Form B

| Chemical Shift [ppm] | Intensity |
|---|---|
| shoulder | |
| 42.5 | 1.4 |
| 35.2 | 2.6 |
| 32.4 | 2.68 |
| 31.6 | 12 |

Form B displays characteristic chemical shifts at 155.4, 146.2, 144.3, 116.6, 42.5 and 35.2 ppm.

TABLE 9

$^{13}$C SSNMR data for amorphous material

| Chemical Shift [ppm] | Intensity |
|---|---|
| 162.1 | 1.46 |
| 154.9 shoulder | — |
| 153.8 | 1.99 |
| 149.0 | 2.98 |
| 146.4 | 1.86 |
| 144.4 shoulder | — |
| 137.4 shoulder | — |
| 130.9 | 8.92 |
| 129.3 shoulder | — |
| 128.4 shoulder | — |
| 127.0 shoulder | — |
| 125.6 shoulder | — |
| 121.0 shoulder | — |
| 116.7 | 2.68 |
| 102.7 | 0.07 |
| 91.6 | 0.05 |
| 61.0 | 1.37 |
| 42.4 | 1.37 |
| 35.3 | 0.59 |
| 32.6 shoulder | — |
| 30.9 | 12 |

The amorphous form displays characteristic chemical shifts at 153.8, 149.0, 130.9, 116.7 and 30.9 ppm.

Stability Data

A low energy screen was carried using N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea form B to investigate whether it is the lowest energy form of the compound. Samples of form B were slurried for 2 weeks in various solvents at 4° C., room temperature (~22° C.) and 40° C. Analysis of wet and dried slurries was carried out at after 2 weeks and 4 months using PXRD. All remained as Form B. Solvent systems used include dimethylacetamide, N-methyl-Pyrrolidine and pyridine.

A hydrate screen was conducted by slurrying samples of form B for 2 weeks at 4° C., room temperature (~22° C.) and 40° C. in aqueous pyridine. The three solvent systems selected contained 50%, 75% and 90% water. No hydrated forms were observed. No change in crystalline form was detected.

The invention claimed is:

1. Polymorphic form B of N-[3-tert-butyl-1-(3-chloro-4-hydroxyphenyl)-1H-pyrazol-5-yl]-N'-{2-[(3-{2-[(2-hydroxyethyl)sulfanyl]phenyl}[1,2,4]triazolo[4,3-a]pyridin-6-yl)sulfanyl]benzyl}urea having shifts at about 155.4, 146.2, 144.3, 116.6, 42.5 and 35.2 ppm when characterised by $^{13}$C solid state NMR referenced to an external standard of crystalline adamantane, setting its upfield resonance to 29.5 ppm.

2. A pharmaceutical composition comprising the polymorphic form B of claim 1 and a pharmaceutically acceptable excipient.

3. A method of treating a TNF-mediated or p38-mediated disease in a mammal comprising administering to the mammal in need thereof a therapeutically effective amount of the polymorphic form B of claim 1, wherein the disease is chronic obstructive pulmonary disease.

4. A combination of the polymorphic form B of claim 1 and a second pharmacologically active substance.

* * * * *